(12) United States Patent
Shin et al.

(10) Patent No.: US 8,440,669 B2
(45) Date of Patent: May 14, 2013

(54) PHARMACEUTICAL COMPOSITION FOR PREVENTION AND TREATMENT OF DIABETES OR OBESITY COMPRISING A COMPOUND THAT INHIBITS ACTIVITY OF DIPEPTIDYL PEPTIDASE-IV, AND OTHER ANTIDIABETIC OR ANTIOBESITY AGENTS AS ACTIVE INGREDIENTS

(75) Inventors: Chang Yell Shin, Seoul (KR); Song-Hyen Choi, Suwon-si (KR); Yu Na Chae, Yongin-si (KR); Eun Kyoung Yang, Yongin-si (KR); Gook Jun Ahn, Anseong-si (KR); Moon-Ho Son, Suwon-si (KR); Heung Jae Kim, Seongnam-si (KR); Woo Young Kwak, Yongin-si (KR); Jong Pil Min, Yongin-si (KR); Tae Hyun Yoon, Yongin-si (KR); Soon Hoe Kim, Suwon-si (KR); Moohi Yoo, Seoul (KR)

(73) Assignee: Dong-A Pharmaceutical Co. Ltd., Seoul (KR)

( * ) Notice: Subject to any disclaimer, the term of this patent is extended or adjusted under 35 U.S.C. 154(b) by 129 days.

(21) Appl. No.: 13/124,150

(22) PCT Filed: Oct. 16, 2009

(86) PCT No.: PCT/KR2009/005970
§ 371 (c)(1),
(2), (4) Date: Apr. 14, 2011

(87) PCT Pub. No.: WO2010/044637
PCT Pub. Date: Apr. 22, 2010

(65) Prior Publication Data
US 2011/0201624 A1   Aug. 18, 2011

(30) Foreign Application Priority Data
Oct. 17, 2008   (KR) ................ 10-2008-0101932

(51) Int. Cl.
*A01N 43/60* (2006.01)
*A61K 31/50* (2006.01)
*A61K 31/497* (2006.01)

(52) U.S. Cl.
USPC ....... 514/249; 514/252.11; 514/866; 514/909

(58) Field of Classification Search .......... 514/249, 514/252.11, 866, 909
See application file for complete search history.

(56) References Cited

FOREIGN PATENT DOCUMENTS

| KR | 2003-0019440 A | 3/2003 |
|---|---|---|
| WO | 2004/052362 A1 | 6/2004 |
| WO | 2006/119260 A2 | 11/2006 |
| WO | 2006/135693 A2 | 12/2006 |
| WO | 2007/041053 A2 | 4/2007 |
| WO | 2007/074884 A1 | 7/2007 |
| WO | 2007/078726 A2 | 7/2007 |

OTHER PUBLICATIONS

Dooseop et al., "Discovery of Potent and Selective Dipeptidyl Peptidase IV Inhibitors Derived from β-Aminoamides Bearing Subsituted Triazolopiperazines" J. Med. Chem., 2008, 51, pp. 589-602.
Lie et al., "Characterization of two cyclic metabolites of sitagliptin" Drug Metabolism and Disposition, vol. 35, No. 4, 2007, pp. 521-524.
Yamazaki et al., "Effects of the combination of a dipeptidyl peptidase IV inhibitor and an insulin secretagogue on glucose and insulin levels in mice and rats" J. Pharmacol Exp Ther. Feb. 2007;320(2):738-46.
Roy et al., "Combination of dipeptidylpeptidase IV inhibitor and low dose thiazolidinedione: preclinical efficacy and safety in db/db mice" Life Sci. Jun. 13, 2007;81(1):72-9.
Yasuda et al., "Metformin Causes Reduction of Food Intake and Body Weight Gain and Improvement of Glucose Intolerance in Combination with Dipeptidyl Peptidase IV Inhibitor in Zucker fa/fa Rats" J. Pharmacol Exp Ther. 2004 310(2):614-619.
Yamazaki et al., "Comparison of efficacies of a dipeptidyl peptidase IV inhibitor and alpha-glucosidase inhibitors in oral carbohydrate and meal tolerance tests and the effects of their combination in mice" J Pharmacol Sci. May 2007;104(1):29-38.

*Primary Examiner* — Renee Claytor
(74) *Attorney, Agent, or Firm* — Lucas & Mercanti, LLP

(57) ABSTRACT

The present invention relates to a pharmaceutical composition for the prevention and treatment of diabetes or obesity comprising as active ingredients a compound which inhibits the activity of dipeptidyl peptidase-IV (DPP-IV), a pharmaceutically acceptable salt thereof, a hydrate thereof, or a solvate thereof, and one or more other antidiabetic or antiobesity agents. The pharmaceutical composition exhibits excellent glucose tolerance and may be useful in the prevention and treatment of diabetes, obesity, and the like by effectively inhibiting blood glucose levels and reducing fat mass.

25 Claims, 8 Drawing Sheets

PHARMACEUTICAL COMPOSITION FOR PREVENTION AND TREATMENT OF DIABETES OR OBESITY COMPRISING A COMPOUND THAT INHIBITS ACTIVITY OF DIPEPTIDYL PEPTIDASE-IV, AND OTHER ANTIDIABETIC OR ANTIOBESITY AGENTS AS ACTIVE INGREDIENTS

CROSS-REFERENCE TO RELATED APPLICATIONS

This application is a 371 of PCT/KR2009/005970 filed on Oct. 16, 2009, which claims the benefit of Korean Patent Application No. 10-2008-0101932 filed on Oct. 17, 2008, the contents of each of which are incorporated herein by reference.

TECHNICAL FIELD

The present invention relates to a pharmaceutical composition for the prevention and treatment of diabetes or obesity comprising as active ingredients a compound which inhibits the activity of dipeptidyl peptidase-IV (DPP-IV), a pharmaceutically acceptable salt thereof, a hydrate thereof, or a solvate thereof, and one or more other antidiabetic or antiobesity agents.

BACKGROUND OF THE INVENTION

Dipeptididyl peptidase-IV (Hereinafter, referred to as DPP-IV) is an enzyme that is generally identified as EC 3.4.14.5 by enzyme classification, functionally belongs to serine protease (Barrett A. J. et al, Arch. Biochem. Biophys., 1995, 247-250), and cleaves the N-terminal dipeptide from peptides that begin with the sequence H-Xaa-Pro-Y (or H-Xaa-Ala-Y wherein Xaa represents any lipophilic amino acid, Pro represents proline, and Ala represents alanine) (Heins J., et al., Biochim. et Biophys. Acta 1988, 161), and is also known as DP-IV, DP-4, or DAP-IV. The enzyme is widely distributed and found in a variety of mammalian tissues such as kidney, liver and small intestine (Hegen M. et al., J. Immunol., 1990, 2908-2914). DPP-IV was first identified as a membrane-bound protein. More recently, a soluble form thereof has been identified (Duke-Cohan J. S. et al., J. Biol. Chem., 1995, 14107-14114). According to studies and reports that have been recently published, it was revealed that such a soluble form of DPP-IV has the same structure and function as a membrane-bound form of the enzyme and is found without a certain membrane-bound domain in blood (Christine D. et. al, Eur. J. Biochem., 2000, 5608-5613).

Initial interest in DPP-IV has focused on its role in the activation of T lymphocytes. DPP-IV responsible for the activation of T lymphocytes was specifically designated as CD26. With the report showing that CD26 binds to or interacts with human immunodeficiency virus (HIV) (Guteil W. G. et al, Proc. Natl. Acad. Sci., 1994, 6594-6598), it was proposed that DPP-IV inhibitors could be useful in the treatment of AIDS (Doreen M. A. et al., Bioorg. Med. Chem. Lett., 1996, 2745-2748).

In addition to a critical role participating in the immune system, the main function of DPP-IV stems from its peptidolytic activity as described above. Attention was particularly given to the role of DPP-IV as it is found that DPP-IV is a key enzyme implicated in the degradation of glucagon-like protein-1 (hereinafter, referred to as "GLP-1") in the small intestine (Mentlein R. et al., Eur. J. Biochem., 1993, 829-835). GLP-1 is a 30 amino-acid peptide hormone which is secreted by intestinal L cells as a response to food intake of the small intestine (Goke R. et. al, J. Biol. Chem., 1993, 19650-19655). Since this hormone is known to have potentiating effects on the action of insulin in the control of postprandial blood glucose levels (Hoist J. J. et al., Diabetes Care, 1996, 580-586), it was postulated that DPP-IV inhibitors might also be usefully employed in the treatment of type 2 diabetes. Based on this assumption, an early form of the DPP-IV inhibitor was developed with some reports demonstrating the therapeutic effectiveness of a medicine in animal experiments (Pauly R. P. et al., Metabolism, 1999, 385-389). Further, DPP-IV-deficient mice or rats maintained GLP-1 activity and high insulin levels, resulting in decreased blood glucose levels and such a genetic disruption or mutation of the DPP-IV gene exhibited no significant effect on the survival of individual animals (Marguet D. et al., Proc. Natl. Acad. Sci., 2000, 6874-6879). As a consequence, it was proposed that DPP-IV is feasible as a potent therapeutic agent for the treatment of type 2 diabetes, which resulted in accelerated research and development of the DPP-IV inhibitor.

Binding of GLP-1 with a receptor in a variety of tissues results in satiety (feelings of fullness), delayed gastric emptying, and facilitated growth of pancreatic beta-cells. Therefore, clinical trials for the treatment of the type 2 diabetes as described above are gradually increasing through intravenous administration of GLP-1 per se (Verdich C. et al, J. Clin. Endocrinol. Metab., 2001, 4382-4389). An in vivo half-life of GLP-1 is merely 2 min (Kieffer T. J., et al., Endocrinology, 1995, 3585-3596), so such a short half-life is a major obstacle to direct use of GLP-1 as a therapeutic agent. Since then, numerous research groups and institutions have made many attempts toward derivatization of GLP-1, resulting in development and commercialization of a peptide which is capable of protracting the short in vivo half-life (Deacon C. F., Diabetes, 2004, 2181-2189). However, such a GLP-1 derivative still suffers from a fundamental limitation in that it is an injectable formulation. Further, a great deal of interest has been increasingly focused on development of an efficient DPP-IV inhibitor, due to the fact that active GLP-1 (7-36) is degraded by DPP-IV and then converted into inactive GLP-1 (9-36) only within a short period of time, e.g. 2 min.

The beginning in the development of DPP-IV inhibitors was similar to the development trend of other inhibitors. That is, most of the research results were for substrate analogues. A representative one of these substrate analogues is a dipeptide derivative which was obtained as the product of the early research which was performed on a parent nucleus having a structure similar to that of Proline (Pro), based on the fact that DPP-IV exhibits pronounced affinity for a peptide containing a certain amino acid Proline (Chinnaswamy T. et al, J. Biol. Chem., 1990, 1476-1483). Typical examples of Proline-like structures include pyrrolidide and thiazolidide, and derivatives containing these parent nucleus compounds exhibit reversible and competitive inhibitory activity for the DPP-IV enzyme (Augustyns K J L., et al, Eur. J. Med. Chem., 1997, 301-309). Among products of such extensive research and development, there are continuing experiments on the action mechanism and efficacy of certain compounds, specifically Val-Pyr (Valine-Pyrrolidide), Ile-Thia (Isoleucine-Thiazolidide), and the like. Particularly, a great deal of attention has been focused on Ile-Thia, because the Val-Pyr structure exhibited relatively poor inhibitory activity on DPP-IV (Hanne B. R., et al, Nat. Struct. Biol., 2003, 19-25), which as such prompted intensive research and study on derivatives of the Ile-Thia compound.

Out of the derivative compounds focused and obtained by the above-mentioned research and study, a compound having the most prominent activity was beta-amino acid thiazolidide series which was attempted to be developed by Merck & Co., Inc. However, according to the results of pharmacodynamic and pharmacokinetic experiments performed in rats, the obtained compound exhibited significantly low bioavailability in conjunction with an apparent limitation in the inhibition of enzymatic activity (Jinyou Xu, et al, Bioorg. Med. Chem. Lett., 2004, 4759-4762). As a consequence, further development on compounds of this series was discontinued due to profound disadvantages.

During the above-mentioned investigation, Merck noticed that a beta-amino acid, in addition to a thiazolidide parent nucleus, is also a key factor having significant effects on the DPP-IV inhibitory activity. This finding was applied to the approach for substitution of the thiazolidide parent nucleus with a different parent nucleus compound (Linda L. B., et al, Bioorg. Med. Chem. Lett., 2004, 4763-4766). With such a subsequent research, a variety of derivatives having substitution of the thiazolidide parent nucleus with a piperazine parent nucleus were synthesized with drug efficacy testing and pharmacodynamic studies. Unfortunately, the piperazine derivatives of Merck still suffered from significantly poor bioavailability. According to the compound optimization to cope with such a disadvantage, sitagliptin, the product MK-0431 (trade name: JANUVIA), was developed with modification of a piperazine moiety to a triazolopiperazine moiety. This product is now commercially available under new drug approval by US FDA in 2006.

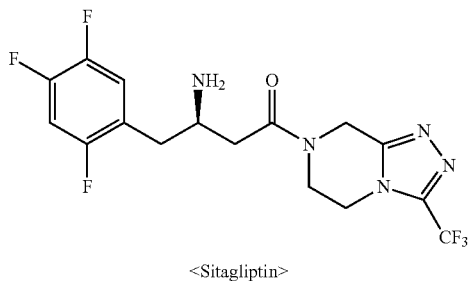 [SMILES: N[C@@H](CC(=O)N1CCn2c(nnc2C(F)(F)F)C1)Cc1cc(F)c(F)cc1F]

<Sitagliptin>

Thus, the present inventors discovered that when a substitution including a hetero atom is made on a piperazinone moiety, the thus-modified compound not only has excellent DPP-IV inhibitory activity, but also is capable of achieving significantly improved bioavailability as compared to conventional DPP-IV inhibitors, then succeeded in synthesis of a novel heterocyclic compound containing a beta-amino group, and completed an invention of a compound represented by the following Formula 1. Based on this, its application was filed as Korea Patent Application No. 2007-0038462.

<Formula 1>

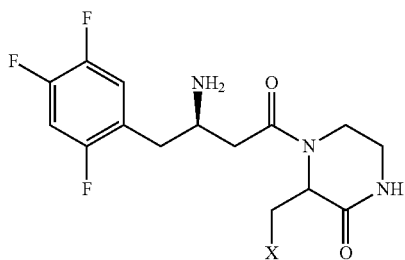

(In formula 1, X is $OR^1$, $SR^1$, or $NR^1R^2$, wherein $R^1$ and $R^2$ are independently a $C_1$~$C_5$ lower alkyl, or $R^1$ and $R^2$ of $NR^1R^2$ may form a 5-membered to 7-membered ring containing a hetero element of O.)

In addition to DPP-IV inhibitors which are currently under active development, diabetes or obesity therapeutic agents which are clinically used or under development include α-glucosidase inhibitors, Biguanides, insulin secretagogues, insulin sensitizers, cannabinoid receptor-1 antagonists, and the like.

α-glucosidase inhibitors exhibit the action of delaying the absorption of carbohydrate from the small intestine and include acarbose, voglibose, emiglitate, miglitol, and the like. Examples of biguanides include metformin, phenformin, or buformin. Insulin secretagogues may be divided into sulfonylurea and non-sulfonylurea species. Examples of sulfonylurea species include glybenclamide (glyburide), glipizide, gliclazide, glimepiride, tolazamide, tolbutamide, acetohexamide, carbutamide, chlorpropamide, glibornuride, gliquidone, glisentide, glisolamide, glisoxepide, glyclopyamide, glycylamide, glipentide, and the like. Examples of non-sulfonylurea species include repaglinide, nateglinide, and the like.

Metformin, a representative Biguanide, is a hypoglycemic agent that regulates high blood glucose levels without stimulating insulin secretion from the pancreas, and is advantageous in that it the drug may be applied to obese diabetic patients because metformin is not associated with weight gain and applied also to patients which are not susceptible to sulfonylurea drugs due to its different action mechanism. Although the action mechanism of metformin is not clearly known, the drug only reduces blood glucose levels of diabetic patients without affecting blood glucose levels of normal subjects, and does not have any action of stimulating β-cells in the pancreas to stimulate insulin secretion compared to sulfonylurea drugs. It is known that metformin increases the action of insulin in peripheral cells, such as liver and muscles and decreases glucose production from the liver, and it was reported in some studies that metformin acts in skeletal muscles and increases the movement of glucose through a cell membrane. In addition, the drug is characterized by improving dyslipidemia to lower blood LDL-cholesterol and triglyceride levels. Clinically, metformin may be administered in a relatively high dose, up to 200 mg per day, and twice a day, for example, morning and evening. When metformin is administered in excess of 2000 mg, it is administered with meal three times a day and the maximum dose per day is 2500 mg.

When metformin is applied to overweight diabetic patients, it is evaluated as an excellent diabetes therapeutic agent. However, care should be taken because adverse side effects may be accompanied by gastrointestinal system disorders, such as diarrhea, nausea, vomiting, and the like, blood system disorders, such as Vitamin B12 deficiency and the like, lactic acidosis which is a severe metabolic complication that is scarce but may lead to 50% mortality by internal accumulation of metformin, and the like.

Insulin sensitizers are relatively recently developed drugs, have a thazolidin-dione (TZD) structure, and act on peroxisome proliferator-activated receptors (PPARs). Examples of insulin sensitizers include troglitazone, ciglitazone, rosiglitazone (AVNADIA), pioglitazone (ACTOS), englitazone, and the like. Besides them, various studies are underway.

Cannabinoid receptor-1 antagonists are relatively recently developed drug targets, inhibit excessive activity of endocannabinoid to regulate the balance of body weight and energy as well as glucose and lipid metabolism, and act on cannabinoid receptor-1 (CB1 receptor) present in central and peripheral nervous systems.

Examples of cannabinoid receptor-1 antagonists include Rimonabant (ACOMPLIA), Otenabant, Ibinabant, Surinabant, and the like. Besides them, various studies are underway.

However, because diabetes or obesity is a chronic disease and its conditions are complicated, there are many cases in which symptoms of the disease are in progress, accompanied by various complications. Therefore, it is necessary to choose a medication most appropriate for the individual patient's conditions. When individual medications are administered alone, there are cases in which sufficient effects may be obtained according to its symptoms. In addition, there are many cases in which it is difficult in clinical practice to choose a medication due to many problems such as increase in dose or occurrence of adverse side effects resulting from prolonged administration. Thus, instead of methods for administering a single drug, various methods for administering one or more drugs with different mechanisms in combination have been recently suggested.

In particular, studies on literatures of combined administration of DPP-IV inhibitors and conventional diabetes therapeutic agents show that a pharmaceutical composition prepared by mixing 3~20% (w/w) of sitagliptin, 25~94% (w/w) of metformin, 0.1~10% (w/w) of a lubricant, and 0~35% (w/w) of a binder is disclosed. In the case of vidagliptin which is a compound commercially available as a trade name of Galvus from Novartis, combined pills of vildagliptin and metformin at ratios of 50~98%, 60~98%, 70~98%, or 80~98% are disclosed in International Publication Gazette WO 07/078,726, and combined pills of vidagliptin and pioglitazone, a PPAR agonist, by direct compression method are described in International Publication Gazette WO 06/135693. However, these literatures describe pharmaceutically optimal composition ratios in a preparation including a DPP-IV inhibitor and metformin or a PPAR agonist, rather than synergistic effects of the two drugs.

In addition, it is described in JPET (2004), 310, 614-619 that a DPP-IV inhibitor valine-pyrrolidide (val-pyr), when administered to an animal in combination with metformin, increased glucagon-like protein levels, decreased food intake and weight gain, and synergistically improved glucose tolerance.

It is disclosed in Life Science (2007), 81, 72-79 that combined administration of vildagliptin and rosiglitazone brought about significant improvement in serum glucose, triglyceride, and glucose tolerances, and pre-existing adverse side effects such as edema from rosiglitazone and the like were alleviated by combined administration of vildagliptin.

It is identified in International Publication Gazette WO 04/052362 that as a result of a glucose tolerance test on vildagliptin and a PPAR agonist micronized fenofibrate, the area under curve (AUC) was decreased by 18% with a single administration of vildagliptin and by 7% with a single administration of fenofibrate while the AUC was decreased by 33%, insulin sensitivity was improved, and weight gain was reduced with a combined administration of the two drugs.

It is mentioned in J. Pharmacol Sci. (2007), 104, 29-38 that postprandial high blood glucose levels are effectively decreased with a combined administration of E3024 which is a DPP-IV inhibitor, voglibose which is an α-glucosidase inhibitor, and acarbose, and in JPET (2007), 320(2), 738-746 that when E3024 is administered in combination with glybenclamide or nateglinide, which is a kind of insulin secretagogue, postprandial high glucose levels are also effectively decreased.

It is mentioned in Korea Patent Publication No. 2003-0019440 that when a compound described in International Publication Gazette WO 99/061431 is administered in combination with a conventional diabetes therapeutic agent, the plasma DPP-IV activity, hemoglobin concentration (HbAlC, %), and plasma glucose are significantly reduced.

It is described in International Publication Gazette WO 07/074,884 that when alogliptin is administered in combination with voglibose, pioglitazone, and the like, pancreas protective effects are enhanced.

It is mentioned in International Publication Gazette WO 07/006,769 that vildagliptin and rimonabant, which are cannabinoid receptor-1 antagonists, are administered in combination, blood glucose and lipid levels and weight are effectively improved, and described in WO 06/119260 that when sitagliptin and a cannabinoid receptor-1 antagonist are administered in combination, glucose tolerance and insulin resistance are improved.

Thus, the present inventors have developed a compound of Formula 1, which is a novel DPP-IV inhibitor, discovered that when the compound is administered in combination with an antidiabetic or antiobesity agent, an excellent glucose tolerance is exhibited, blood glucose levels are effectively inhibited, and fat mass is reduced, thereby leading to completion of the present invention.

SUMMARY OF THE INVENTION

Technical Problem

An object of the present invention is to provide a pharmaceutical composition for the prevention and treatment of diabetes or obesity comprising as active ingredients a compound which inhibits the activity of dipeptidyl peptidase-IV and other antidiabetic or antiobesity agents.

Technical Solution

According to the present invention, a pharmaceutical composition for the prevention and treatment of diabetes or obesity comprising as active ingredients (1) a compound represented by the following Formula 1, a pharmaceutically acceptable salt thereof, a hydrate thereof, or a solvate thereof, and (2) one or more other antidiabetic or antiobesity agents.

<Formula 1>

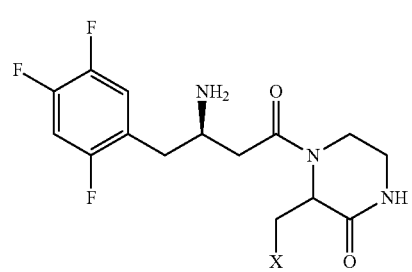

(In Formula 1, X is as Defined Herein.)

Advantageous Effects

According to the present invention, a pharmaceutical composition comprising as active ingredients a compound which is a kind of a novel DPP-IV inhibitor and one or more other antidiabetic or antiobesity agents may be useful in the prevention and treatment of diabetes, obesity, and the like by administering the composition to enhance glucose tolerance effects, inhibition of blood glucose levels, and reducing effects of fat mass, compared to other conventional antidiabetic or antiobesity agents.

DETAILED DESCRIPTION OF THE INVENTION

Figure 1:
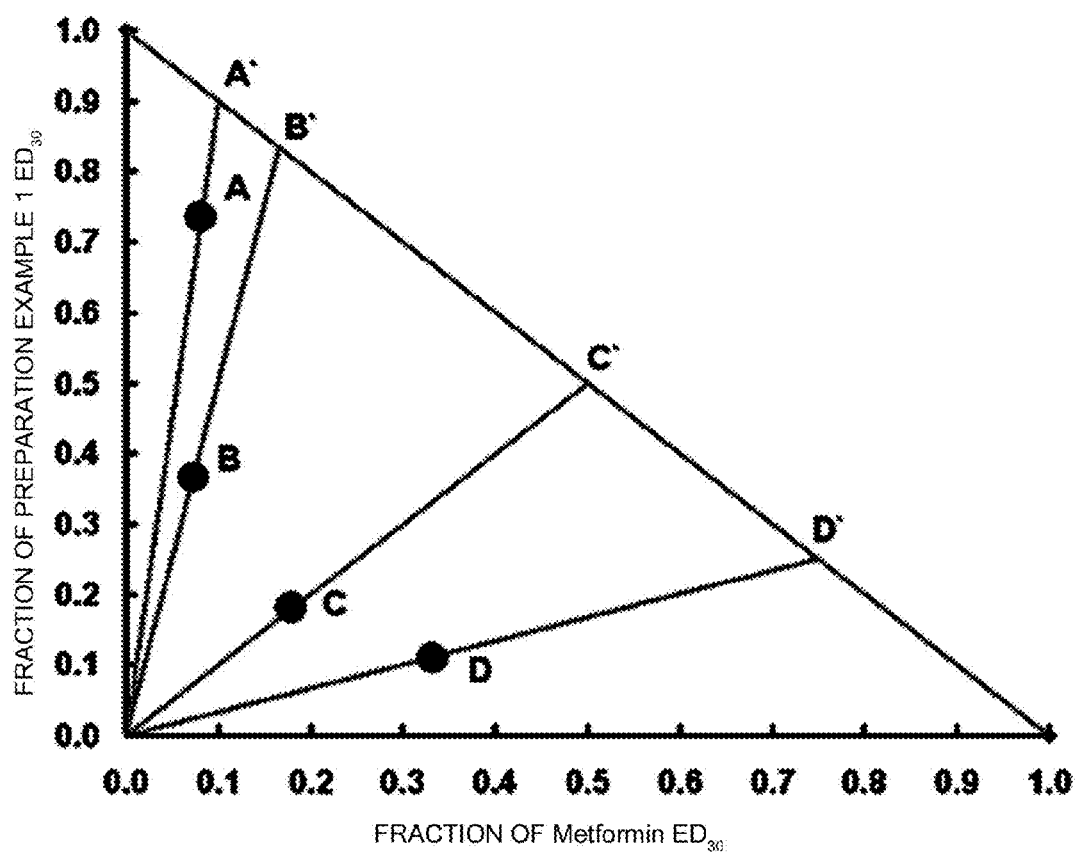
FIG. 1 is an isobologram showing antidiabetic effects of mixed compositions containing a compound of Formula 1 and metformin.

Hereinafter, the present invention will be described in detail.

The present invention provides a pharmaceutical composition for the prevention and treatment of diabetes or obesity comprising as active ingredients (1) a compound represented by the following Formula 1, a pharmaceutically acceptable salt thereof, a hydrate thereof, or a solvate thereof, and (2) one or more other antidiabetic or antiobesity agents.

<Formula 1>

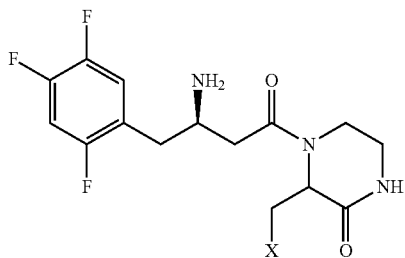

In Formula 1,
X is $OR^1$, $SR^1$, or $NR^1R^2$,

Wherein $R^1$ and $R^2$ are independently a $C_1$~$C_5$ lower alkyl, or $R^1$ and $R^2$ of $NR^1R^2$ may form a 5-membered to 7-membered ring containing a hetero element of O.

The $C_1$~$C_5$ lower alkyl in Formula 1 may include a $C_1$ to $C_5$ alkyl and a cycloalkyl.

The compound represented by Formula 1 may have two asymmetric centers, and thus may have asymmetric centers at the β-carbon and at the carbon of 3-position of piperazine. Therefore, the center may be present in the form of a single diastereomer, racemate, racemic mixture or diastereoisomeric mixture, all of which may be included in the compound represented by Formula 1 according to the present invention.

In addition, the compound represented by Formula 1 of the present invention may be partially present as a tautomer, and individual tautomers as well as mixtures thereof may be included in the compound of the present invention.

The stereomer of the present invention may be obtained by stereoselective synthesis according to a conventional method known in the art, using an optically pure starting material or a known reagent.

Preferable examples of the compound represented by Formula 1 of the present invention are as follows.

1) (R)-4-[(R)-3-amino-4-(2,4,5-trifluorophenyl)butanoyl]-3-(t-butoxymethyl)piperazin-2-one;
2) (S)-4-[(R)-3-amino-4-(2,4,5-trifluorophenyl)butanoyl]-3-(t-butoxymethyl)piperazin-2-one;
3) (R)-4-[(R)-3-amino-4-(2,4,5-trifluorophenyl)butanoyl]-3-(methoxymethyl)piperazin-2-one;
4) (R)-4-[(R)-3-amino-4-(2,4,5-trifluorophenyl)butanoyl]-3-(isopropoxymethyl)piperazin-2-one;
5) (R)-4-[(R)-3-amino-4-(2,4,5-trifluorophenyl)butanoyl]-3-(cyclopentyloxymethyl)piperazin-2-one;
6) (R)-4-[(R)-3-amino-4-(2,4,5-trifluorophenyl)butanoyl]-3-[(diethylamino)methyl]piperazin-2-one;
7) (R)-4-[(R)-3-amino-4-(2,4,5-trifluorophenyl)butanoyl]-3-[(ethylmethylamino)methyl]piperazin-2-one;
8) (R)-4-[(R)-3-amino-4-(2,4,5-trifluorophenyl)butanoyl]-3-(morpholinomethyl)piperazin-2-one;
9) (R)-4-[(R)-3-amino-4-(2,4,5-trifluorophenyl)butanoyl]-3-(t-butylthiomethyl)piperazin-2-one.

The pharmaceutically acceptable salt of the beta-amino group-containing hetero compound of Formula 1 according to the present invention may be prepared by any conventional method for preparation of salts known in the art.

As used herein, the term "pharmaceutically acceptable salt" refers to a salt prepared from a pharmaceutically acceptable non-toxic base or acid including an inorganic or organic base and an inorganic or organic acid. Examples of the salt derived from an inorganic base include aluminum, ammonium, calcium, copper, ferric, ferrous, lithium, magnesium, manganate, manganese, potassium, sodium, zinc, and the like. Particularly preferred are ammonium, calcium, magnesium, potassium and sodium salts. A solid salt may have one or more crystal structures, or otherwise may be in the form of a hydrate. Examples of the salt derived from a pharmaceutically acceptable non-toxic organic base include a primary, secondary or tertiary amine, a substituted amine such as a naturally-occurring substituted amine, a cyclic amine, or a basic ion exchange resin such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resin, procaine, purine, theobromine, triethylamine, trimethylamine, tripropylamine, tromethamine, and the like.

When the compound of the present invention is basic, a salt thereof may be prepared from pharmaceutically acceptable non-toxic acids including inorganic and organic acids. Examples of the acid include acetic acid, benzenesulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid, p-toluene sulfonic acid, adipic acid, and the like. Preferably, the pharmaceutically acceptable salt may be acetic, citric, hydrochloric, malic, phosphoric, succinic, tartaric and adipic acids. More preferably, the pharmaceutically acceptable salt may be tartaric acid.

As used herein, the compound of Formula 1 designated is intended to embrace a pharmaceutically acceptable salt thereof.

A hydrate of a compound of Formula 1 of the present invention or a pharmaceutically acceptable salt thereof is intended to embrace a stoichiometric or non-stoichiometric amount of water bound thereto by non-covalent intermolecular forces. The hydrate may contain 1 or more equivalent of water, typically 1 to equivalents of water. The hydrate may be prepared by crystallization of the compound of Formula 1 of the present invention or a pharmaceutically acceptable salt thereof in water or water-containing solvent.

A solvate of a compound of Formula 1 of the present invention or a pharmaceutically acceptable salt thereof is intended to embrace a stoichiometric or non-stoichiometric amount of a solvent bound thereto by non-covalent intermolecular forces. Preferred solvents are volatile, non-toxic, and suitable for administration to humans. For example, mention may be made of ethanol, methanol, propanol, methylene chloride, and the like.

A compound of Formula 1 of the present invention may be readily obtained as described in Korea Patent Application No. 2007-0038462. Specifically, (R)-(3-t-butoxymethyl)piperazin-2-one synthesized from 1) (3R)-t-butoxycarbonylamino-4-(2,4,5-trifluorophenyl)butanoic acid and D-serine methyl ester as starting materials may be synthesized into an intermediate t-butyl (R)-4[(R)-2-(t-butoxymethyl)-3-oxopiperazin-1-yl]-4-oxo-1-(2,4,5-trifluorophenyl)-butan-2-ylcarbamate by standard peptidization reaction (step 1), and then subjected to deprotection (step 2), followed by neutralization to obtain a compound in the form of Formula 1.

The compound of Formula 1 is a kind of DPP-IV inhibitor, exhibits excellent inhibitory activity on DPP-IV and bioavailability, and may be useful in the prevention and treatment of diseases such as diabetes, obesity, and the like, caused by DPP-IV.

An antidiabetic or antiobesity agent which is mixed with a compound represented by Formula 1 in the present invention to provide a composition for prevention and treatment of diabetes or obesity may be preferably selected from the group consisting of α-glucosidase inhibitor, Biguanide, insulin secretagogue, insulin sensitizer, and cannabinoid receptor-1 antagonist. However, it is not limited thereto.

The Biguanide of the present invention refers to a drug including a biaguanid structure and having effects, such as anaerobic glycolysis promoting effects, enhancement of peripheral insulin effects, suppression of absorption of glucose from the intestinal tract, and suppression of liver glyconeogenesis. The Biaguanide may be selected from the group consisting of metformin, buformine, and phenformin, but it is not limited thereto.

The insulin sensitizer of the present invention refers to a drug which improves insulin action dysfunction to lower blood glucose levels, commonly has a thiazolidindione (TZD) structure, and acts on peroxisome proliferator-activated receptors (PRARs). The insulin sensitizer may be selected from the group consisting of troglitazone, ciglitazone, rosiglitazone (AVNADIA), pioglitazone (ACTOS), and englitazone, but it is not limited thereto.

The insulin secretagogue of the present invention refers to a drug promoting insulin secretion from beta-cells of the pancreas, and may be a drug having a sulfonyl urea or non-sulfonylurea structure. Preferably, the insulin secretagogue may be a drug having a sulfonyl urea structure, selected from the group consisting of glybenclamide (glyburide), glipizide, gliclazide, glimepiride, tolazamide, tolbutamide, acetohexamide, carbutamide, chlorpropamide, glibornuride, gliquidone, glisentide, glisolamide, glisoxepide, glyclopyamide, glycylamide, and glipentide, or a drug having a non-sulfonylurea structure, such as repaglinide or nateglinide, but it is not limited thereto.

The α-glucosidase inhibitor of the present invention refers to a drug competitively inhibiting α-glucosidase which is a type of digestive enzyme in gut to suppress digestion and absorption of starch, disaccharides, and the like. The α-glucosidase inhibitor may be selected from the group consisting of acarbose, voglibose, emiglitate, and miglitol, but it is not limited thereto.

The cannabinoid receptor-1 antagonist of the present invention refers to a drug inhibiting excessive activity of endocannabinoid to regulate the balance of body weight and energy as well as glucose and lipid metabolism. The cannabinoid receptor-antagonist may be selected from the group consisting of rimonabant (ACOMPLIA), Otenabant, Ibinabant, and Surinabant, but it is not limited thereto.

The dose or dosage of a pharmaceutical composition according to the present invention varies depending on a patient's body weight, age, sex, health conditions, diet, time of administration, administration method, evacuation rate, the severity of a disease, and the like. The general dosage unit is calculated based on the amount of active ingredient which may be given to a 70 kg human subject in a single dose to judge whether a therapeutically effective dose is attained. However, it will be appreciated that the precise therapeutically effective dose of the active ingredients will vary depending upon the relative amount of each active component being used, upon the particular drug being used and upon the aforementioned synergistic ratios.

The compound of Formula 1 may be preferably included in the pharmaceutical composition in a range of about 0.1 to about 1,500 mg. However, the range may increase or decrease, depending on the symptom.

In addition, a recommended dose well known is suitable as a daily clinical dose of other antidibetic or antiobesity agents included in a pharmaceutical composition of the present invention. For example, a dose of about 500 mg to about 2000 mg is generally known as a daily clinical dose of metformin.

A mixing ratio of a compound represented by Formula 1 included in a pharmaceutical composition of the present invention and other antidibetic or antiobesity agents may be selected in the range of 1:16.7 to 1:450 based on a dose to be administered. Optimal therapeutically effective doses to be administered may be readily determined by those skilled in the art and will vary with the amount of active ingredients used in a synergistic ratio based on a fraction of their respective $ED_{30}$ values, the strength of the preparation, the mode of administration and the advancement of the condition or disorder to be treated. In addition, factors associated with the particular subject being treated, including subject age, body weight, diet and time of administration, will result in the need to adjust the dose to an appropriate therapeutically effective level.

The pharmaceutical composition of the present invention may be administered within the range of a synergistic ratio based on a fraction of their respective $ED_{30}$ values. The $ED_{30}$ value refers to a dose of a pharmaceutical composition, at which 30% of the percent inhibition is exhibited. The percent inhibition may be obtained by calculating an area under curve of an experimental group, except for an area under curve of a group in which glucose has not been administered, in the change curve of blood glucose, comparing the value with that of a control group in which glucose has been administered, and calculating the inhibition ratio. In general, it is suggested that an effective dose is defined as a dose to suppress the AUC by 30% or more in mouse experiments (WO2006/076231 A2).

In the pharmaceutical composition of the present invention, the compound of Formula 1 and Biguanide may be included in the ratio range of 9:1 to 1:3 based on a fraction of their respective $ED_{30}$ values, and more preferably in the ratio of 1:1.

In the pharmaceutical composition of the present invention, when the mixing ratio of the compound of Formula 1 and Biguanide is 1:16.7 or less, or 1:450 or more based on the weight ratio, poor efficacy or adverse side effects may occur. On the contrary, in the range of 1:16.7 to 1:450, synergistic improvement effects in glucose tolerance may occur. Therefore, the two agents may be preferably included in the range of 1:16.7 to 1:450 based on the weight ratio. However, the ratio is not limited thereto.

In the pharmaceutical composition of the present invention, when the mixing ratio of the compound represented by Formula 1 and an insulin sensitizer is 1:0.01 or less, or 1:0.4 or more based on the weight ratio, poor efficacy or adverse side effects may occur because it is a value deviating from a daily clinical dose of the insulin sensitizer. On the contrary, in the range of 1:0.01 to 1:0.4, synergistic improvement effects in efficacy may occur. Therefore, the mixing ratio of the compound 1 and the insulin sensitizer may be preferably in the range of 1:0.01 to 1:0.4 based on the weight ratio. However, the ratio is not limited thereto and may be adjusted depending on the symptoms.

In the pharmaceutical composition of the present invention, when the mixing ratio of the compound of Formula 1 and an insulin secretagogue is 1:0.2 or less, or 1:3.2 or more based on the weight ratio, the dose may exceed a daily clinical dose of the insulin secretagogue or poor efficacy may occur. On the contrary, synergistic improvement effects in efficacy may occur in the range of 1:0.2 to 1:3.2. Therefore, the mixing ratio of the compound 1 and the insulin secretagogue may be preferably in the range of 1:0.2 to 1:3.2. However, the ratio is not limited thereto.

In addition, in the pharmaceutical composition of the present invention, when the mixing ratio of the compound represented by Formula 1 and an α-glucosidase inhibitor is 1:0.03 or less, or 1:0.18 or more based on the weight ratio, the dose may exceed a daily clinical dose of the α-glucosidase inhibitor or poor efficacy may occur. On the contrary, synergistic improvement effects in efficacy may occur in the range of 1:0.03 to 1:0.18. Therefore, it is preferable to have the mixing ratio of the compound 1 and the α-glucosidase inhibitor in the range of 1:0.03 to 1:0.18. However, the ratio is not limited thereto.

In the pharmaceutical composition of the present invention, when the mixing ratio of the compound of Formula 1 and a cannabinoid receptor-1 antagonist is 1:0.1 or less, or 1:1 or more based on the weight ratio, the dose may exceed a daily clinical dose of the cannabinoid receptor-1 antagonist or poor efficacy may occur. Therefore, it is preferable to have the mixing ratio of the compound 1 and the cannabinoid receptor-1 antagonist in the range of 1:1 to 1:10. However, the ratio is not limited thereto.

As used herein, the term "administration" means the introduction of a predetermined material into patients using a suitable method. The composition of the present invention may be orally or parenterally administered via any of the common routes, as long as it is able to reach the desired tissue. Also, the composition may be administered using a certain apparatus capable of transporting active substances into target cells. It is preferable to orally administer the pharmaceutical composition of the present invention, but it is not limited thereto. Parenteral administration includes subcutaneous, intravenous, intramuscular or intrathoracic injections, but is not limited thereto.

The pharmaceutical composition of the present invention may be formulated into various oral or parenteral forms of a broad range during clinical administration and may be administered.

Examples of the dosage form for oral administration may include tablets, pills, hard/soft capsules, solutions, suspensions, emulsions, syrups, granules, elixirs, and the like. These pharmaceutical formulations may contain, in addition to the active ingredient, one or more conventional diluents or excipients, such as fillers, extenders, wetting agents, disintegrants, glidants, binders, surfactants, and the like. Examples of the disintegrants may include agar, starch, alginic acid or a sodium salt thereof, anhydrous calcium monohydrogen phosphate, and the like. Examples of the glidants may include silica, talc, stearic acid or magnesium or calcium salt thereof, polyethylene glycol, and the like. Examples of the binder may include magnesium aluminum silicate, starch paste, gelatin, tragacanth, methylcellulose, sodium carboxymethylcellulose, polyvinylpyrrolidone, low-substituted hydroxypropyl cellulose, and the like. In addition, the pharmaceutical formulation may include diluents, e.g. lactose, dextrose, sucrose, mannitol, sorbitol, cellulose, glycine, and the like. If desired, the formulation may further contain conventionally known effervescent mixtures, absorbents, colorants, flavors, sweeteners, and the like.

Examples of the dosage form for parenteral administration may include sterilized aqueous solutions, non-aqueous solutions, suspensions, emulsions, lyophilized agents, or suppositories. As non-aqueous solvents or suspending agents, propylene glycol, polyethylene glycol, vegetable oils such as olive oil, injectable esters such as ethyl oleate, and the like can be used. As the base of the injectable preparation, conventional additives such as solubilizers, isotonic agents, suspending agents, emulsifying agents, stabilizers and preservatives may be used. The pharmaceutical composition according to an Example of the present invention may be prepared as a solution or suspension by mixing the compound of Formula 1 or a pharmaceutically acceptable salt thereof and metformin with a stabilizer or buffer in water, and may be prepared in a unit dosage form (e.g. ampoule or vial). The composition may be sterilized or contain an adjuvant (e.g., a preservative, a stabilizer, a wetting agent or an emulsifier, a salt for osmotic regulation, a buffering agent, and the like). In addition, the composition may further contain other therapeutically useful substances. The composition may be manufactured in a conventional manner by mixing, granulating or coating methods.

EXAMPLES

Hereinafter, the present invention will be described in more detail with reference to following Preparation Examples, Examples, Experimental Examples, and Preparation Examples. However, the following examples are provided for illustrative purposes only, and the scope of the present invention should not be limited thereto in any manner.

Preparation Example

Preparation of Compound of Formula 1 and Pharmaceutically Acceptable Salts Thereof Preparation Example 1

Preparation of (R)-4-[(R)-3-amino-4-(2,4,5-trifluorophenyl)-butanoyl]-3-(t-butoxymethyl)piperazin-2-one Step 1): Preparation of (R)-methyl 1-trithylaziridine-2-carboxylate 200 g of D-serine methyl ester hydrochloride was added to 1.8 L of chloroform, and the reaction solution was cooled to 0° C., to which 448 mL of triethylamine was then slowly added. 358.4 g of trityl chloride was slowly added to the reaction mixture which was then stirred for 1 hour. The reaction mixture was warmed to room temperature, and 1 L of chloroform was added thereto, followed by washing with 2.5 L of water. The organic layer was dried over magnesium sulfate and again cooled to 0° C., to which 484 mL of triethylamine and 15.7 g of 4-methylaminopyridine were then sequentially and slowly added. The reaction mixture was stirred for 5 min and 139 mL of methane sulfonyl chloride was slowly added thereto. The reaction mixture was warmed to room temperature, stirred for another 4 hours and then refluxed for 12 hours. The reaction mixture was cooled to room temperature, and washed with 4 L of water and then 3 L of brine. The organic layer was dried over magnesium sulfate and concentrated to dryness under reduced pressure. 3 L of ethanol was added to the resulting residue which was then stirred. The resulting solids were filtered to afford 329 g of the title compound.

$^1$H NMR (400 MHz, CDCl$_3$): 7.42~7.49(m, 6H), 7.18~7.32(m, 9H), 7.68(s, 1H), 3.74(s, 3H), 2.24(m, 1H), 1.87(m, 1H), 1.40(m, 1H)

Step 2): Preparation of (R)-1-benzyl 2-methyl aziridine-1,2-dicarboxylate 328.4 g of (R)-methyl 1-tritylaziridine-2-carboxylate was dissolved in 1.4 L of chloroform and the reaction solution was cooled to 0° C., to which 462 mL of trifluoroacetic acid was then slowly added. The reaction mixture was stirred for 1 hour, to which 2 L of water was then added, followed by stirring for 10 min and removal of the organic layer. The aqueous layer was neutralized with sodium hydrogen carbonate and used in subsequent reactions without further purification.

2 L of diethyl ether and 120.5 g of sodium hydrogen carbonate were added to the aqueous layer, and the reaction solution was cooled to 0° C., to which 165 mL of benzyl chloroformate was then slowly added dropwise. The reaction mixture was stirred for another 2 hours and the aqueous layer was removed. The organic layer was dried over magnesium sulfate, concentrated and dried under reduced pressure, and purified by column chromatography, thereby affording 108.5 g of the title compound.

$^1$H NMR (400 MHz, DMSO): 7.32-7.36(m, 5H), 5.13(s, 2H), 3.09(dd, J=3.2, 5.4 Hz, 1H), 2.58(dd, J=1.2, 3.2 Hz, 1H), 2.47(dd, J=1.2, 5.4 Hz, 1H),

Step 3): Preparation of (R)-2-amino-3-t-butoxypropane methyl ester 1.1 g of (R)-1-benzyl 2-methyl aziridine-1,2-dicarboxylate was dissolved in 11 mL of chloroform, to which 18 mL of t-butanol was then added. To the reaction mixture was slowly added dropwise 1.2 mL of BF$_3$OEt$_2$, followed by stirring for 12 hours. The reaction was terminated with addition of 2 L of water to the reaction mixture. Then, the organic layer was separated and dried over magnesium sulfate, concentrated and dried under reduced pressure, and then used in subsequent reactions without further purification.

The resulting residue was dissolved in 10 mL of methanol, to which 740 mg of palladium/carbon in 2 mL of ethyl acetate was then added, followed by hydrogen bubbling for 1 hour under ambient atmospheric pressure. The reaction mixture was filtered and dried under reduced pressure to afford 736 mg of the title compound.

$^1$H NMR (400 MHz, CD3OD): 4.21(m, 1H), 3.82(s, 3H), 3.74~3.88(m, 2H), 1.20(s, 9H)

Step 4): Preparation of (R)-3-t-butoxy-2-(2-(t-butoxycarbonylamino)ethylamino)propionic acid methyl ester 736 mg of (R)-2-amino-3-t-butoxypropane methyl ester prepared in Step 3 was dissolved in 14 mL of dichloromethane, to which 6335 mg of N-t-butoxycarbonyl-2-aminoacetaldehyde methanol was then slowly added. The reaction mixture was cooled to 0° C., followed by gradual addition of 1.2 mL of triethylamine and 1.78 g of sodium triacetoxyborohydride. The reaction mixture was warmed to room temperature, followed by stirring for 12 hours. A saturated sodium hydrogen carbonate solution was added to terminate the reaction, and the organic layer was washed with 10 mL of water and brine, concentrated and dried under reduced pressure. The resulting residue was purified by column chromatography, thereby affording 355 mg of the title compound.

$^1$H NMR (400 MHz, CDCl$_3$): 5.10 (m, 1H), 3.71 (s, 3H), 3.56 (m, 2H), 3.40 (m, 1H), 3.15~3.28 (m, 2H), 2.81 (m, 1H), 2.67 (m, 1H), 1.42 (s, 9H), 1.13 (s, 9H)

Step 5): Preparation of (R)-2-((benzyloxycarbonyl) (2-t-butoxycarbonylamino)ethyl)amino)-3-t-butoxypropionic acid methyl ester 355 mg of (R)-3-t-butoxy-2-(2-(t-butoxycarbonylamino) ethylamino)propionic acid methyl ester prepared in Step 4 was dissolved in 11 mL of tetrahydrofuran, and the reaction mixture was cooled to 0° C., to which 187 mg of sodium hydrogen carbonate was then added. 192 µl of benzylchloroformate was slowly added dropwise thereto, and the reaction mixture was warmed to room temperature. After 12 hours, the reaction mixture was dried under reduced pressure, followed by addition of 10 mL of ethyl acetate, and the organic layer was washed with 10 mL of water. The organic layer was dried over magnesium sulfate, dried under reduced pressure, and purified by column chromatography, thereby affording 410 mg of the title compound.

$^1$H NMR (400 MHz, CDCl$_3$): 7.36~7.25 (m, 5H), 5.82~5.72 (m, 1H), 5.17~5.03 (m, 2H), 4.15 (m, 1H), 3.98 (m,

1H), 3.81 (m, 1H), 3.73 (s, 3H), 3.60 (m, 1H), 3.42~3.28 (m, 3H), 1.40 (s, 9H), 1.14 (s, 9H)

Step 6): Preparation of (R)-benzyl 2-(t-butoxymethyl)-3-oxopiperazine-1-carboxylate 410 mg of (R)-2-((benzyloxycarbonyl) (2-t-butoxycarbonylamino)ethyl)amino)-3-t-butoxypropionic acid methyl ester prepared in Step 5 was dissolved in 10 mL of methanol, and the reaction mixture was cooled to 0° C., to which 4 mL of 2-N hydrochloric acid/diethyl ether was then slowly added, followed by stirring for 3 hours. The reaction mixture was dried under reduced pressure and used in subsequent reactions without further purification.

The resulting residue was dissolved in 10 mL of dichloromethane and the reaction mixture was cooled to 0° C., to which 152 μl of triethylamine was then slowly added. 1.1 mL of trimethylaluminum (2.0 M solution in toluene) was slowly added thereto, and the reaction mixture was warmed to room temperature and then stirred for 12 hours. The reaction mixture was cooled to 0° C. and a saturated ammonium chloride aqueous solution was added to terminate the reaction. 10 mL of ethyl acetate was added to the reaction mixture which was then washed with 10 mL of brine. The organic layer was dried over magnesium sulfate and dried under reduced pressure. The resulting residue was purified by column chromatography to afford 103 mg of the title compound.

$^1$H NMR (400 MHz, CDCl$_3$): 7.34~7.25 (m, 5H), 6.27 (m, 1H), 5.14 (m, 2H), 4.57 (m, 1H), 4.19 (m, 1H), 4.08 (m, 1H), 3.94 (m, 1H), 3.74 (m, 1H), 3.64 (m, 1H), 3.42 (m, 1H), 3.29 (m, 1H), 1.09 (s, 9H)

Step 7): Preparation of (R)-(3-t-butoxymethyl)piperazin-2-one 103 mg of (R)-benzyl 2-(t-butoxymethyl)-3-oxopiperazine-1-carboxylate prepared in Step 6 was dissolved in 2 mL of methanol, to which 50 mg of palladium/carbon in 1 mL of ethyl acetate was then added, followed by hydrogen bubbling for 1 hour under ambient atmospheric pressure. The reaction mixture was filtered and dried under reduced pressure to afford 58 mg of the title compound.

$^1$H NMR (400 MHz, CDCl$_3$): 6.41 (brs, 1H), 3.76 (m, 3H), 3.63 (m, 1H), 3.52 (m, 1H), 3.42 (m, 1H), 3.28 (m, 1H), 3.16 (m, 1H), 2.95 (m, 1H), 2.45 (brs, 1H), 1.17 (s, 9H)

Step 8): Preparation of t-butyl (R)-4-[(R)-2-(t-butoxymethyl)-3-oxopiperazin-1-yl]-4-oxo-1-(2,4,5-trifluorophenyl)butan-2-ylcarbamate 104 mg of (3R)-t-butoxycarbonylamino-4-(2,4,5-trifluorophenyl)butanoic acid and 58 mg of (R)-(3-t-butoxymethyl) piperazin-2-one were added to 4 mL of N,N-dimethylformamide, to which 63 mg of 1-hydroxybenzotriazole (HOBT) and 217 μl of diisopropylethylamine were then added. The reaction mixture was cooled to 0° C. and 78 mg of 1-ethyl-3-(3-dimethylaminopropyl)carbodiimide (EDC) was added thereto, followed by stirring at room temperature for 12 hours. The reaction mixture was diluted with 10 mL of ethyl acetate and washed two times with brine. The organic layer was dried over magnesium sulfate and concentrated. The resulting residue was purified by column chromatography to afford 97 mg of the title compound.

$^1$H NMR (400 MHz, CDCl$_3$): 7.03 (m, 1H), 6.88 (m, 1H), 5.97 (m, 1H), 5.48 (m, 1H), 4.16~4.07 (m, 1H), 4.02~3.91 (m, 1H), 3.74 (m, 2H), 3.37 (m, 2H), 3.24 (m, 1H), 2.92 (m, 2H), 2.80 (m, 1H), 2.59 (m, 2H), 1.34 (d, 9H), 1.13 (s, 9H)

Step 9): Preparation of (R)-4-[(R)-3-amino-4-(2,4,5-trifluorophenyl)butanoyl]-3-(t-butoxymethy)piperazin-2-one 97 mg of t-butyl (R)-4-[(R)-2-(t-butoxymethyl)-3-oxopiperazin-1-yl]-4-oxo-1-(2,4,5-trifluorophenyl)butan-2-ylcarbamate prepared in Step 8 was dissolved in 3 mL of methanol, followed by addition of 2 mL of 2N-hydrochloric acid/diethyl ether and stirring at room temperature for 3 hours.

The reaction mixture was concentrated and dried under reduced pressure, to which 10 mL of 5% sodium hydrogen carbonate aqueous solution was added and 10 mL of dichloromethane/2-propanol (4/1 (v/v)) mixed solution for extraction twice, followed by drying the organic layer under reduced pressure to afford 55 mg of the title compound as a solid.

$^1$H NMR (400 MHz, CD$_3$OD): 7.27 (m, 1H), 7.14 (m, 1H), 4.56~4.39 (m, 1H), 3.96~3.81 (m, 3H), 3.70 (m, 1H), 3.46 (m, 1H), 3.43~3.32 (m, 1H), 2.83~2.65 (m, 3H), 2.58~2.40 (m, 2H), 1.16 (s, 3H), 1.11 (s, 6H)

Preparation Example 2

Preparation of (R)-4-[(R)-3-amino-4-(2,4,5-trifluorophenyl)butanoyl]-3-(methoxymethyl)piperazin-2-one Methanol was used instead of t-butanol in Step 3 of Preparation Example 1, and the title compound was then synthesized similarly to Steps 4 through 9 of Preparation Example 1.

Preparation Example 3

Preparation of (R)-4-[(R)-3-amino-4-(2,4,5-trifluorophenyl)butanoyl]-3-(isopropoxymethyl)piperazin-2-one Isopropanol was used instead of t-butanol in Step 3 of Preparation Example 1, and the title compound was then synthesized similarly to Steps 4 through 9 of Preparation Example 1.

Preparation Example 4

Preparation of (R)-4-[(R)-3-amino-4-(2,4,5-trifluorophenyl)butanoyl]-3-(cyclopentyloxymethyl)piperazin-2-one Cyclopentanol was used instead of t-butanol in Step 3 of Preparation Example 1, and the title compound was then synthesized similarly to Steps 4 through 9 of Preparation Example 1.

Preparation Example 5

Preparation of (R)-4-[(R)-3-amino-4-(2,4,5-trifluorophenyl)butanoyl]-3-[(diethylamino)methyl]piperazin-2-one Diethylamine was added instead of t-butanol and reflux was carried out instead of addition of BF$_3$OEt$_2$ in Step 3 of Preparation Example 1, and the title compound was then synthesized similarly to Steps 4 through 9 of Preparation Example 1.

Preparation Example 6

Preparation of (R)-4-[(R)-3-amino-4-(2,45-trifluorophenyl)butanoyl]-3-[(ethylmethylamino)methyl]piperazin-2-one Ethylmethylamine was added instead of t-butanol and reflux was carried out instead of addition of $BF_3OEt_2$ in Step 3 of Example 1, and the title compound was then synthesized similarly to Steps 4 through 9 of Preparation Example 1.

Preparation Example 7

Preparation of (R)-4-[(R)-3-amino-4-(2,4,5-trifluorophenyl)butanoyl]-3-(morpholinomethyl)piperazin-2-one Morpholine was added instead of t-butanol and reflux was carried out instead of addition of $BF_3OEt_2$ in Step 3 of Preparation Example 1, and the title compound was then synthesized similarly to Steps 4 through 9 of Preparation Example 1.

Preparation Example 8

Preparation of (R)-4-[(R)-3-amino-4-(2,4,5-trifluorophenyl)butanoyl]-3-(t-butylthiomethyl)piperazin-2-one t-butyl thiol was used instead of t-butanol in Step 3 of Preparation Example 1, and the title compound was then synthesized similarly to Steps 4 through 9 of Preparation Example 1.

Preparation Example 9

Preparation of (S)-4-[(R)-3-amino-4-(2,4,5-trifluorophenyl)butanoyl]-3-(t-butoxymethyl)piperazin-2-one L-serine methyl ester hydrochloride was used instead of D-serine methyl ester hydrochloride in Step 1 of Preparation Example 8, and the title compound was then synthesized similarly to Steps 2 through 9 of Preparation Example 8.

Example

Preparation of a Composition Containing a Compound of Formula 1 and an Antidibetic or Antiobesity Drug

Example 1

Preparation of a Mixed Composition of a Compound Represented by Formula 1 and Biguanide

Example 1-1

Preparation of a Pharmaceutical Composition Containing (R)-4-[(R)-3-amino-4-(2,4,5-trifluorophenyl)butanoyl]-3-(t-butoxymethyl)piperazin-2-one(tartrate) and Metformin at a Ratio of 9:1 Based on $ED_{30}$ The compound prepared in Preparation Example 1 and metformin were weighed, and 0.5% methylcellulose was used to prepare 10 mL/kg of a suspension with each composition (0.045~0.36 mg/kg of the compound prepared in Preparation Example 1: 0.75~6 mg/kg of metformin)/10 mL.

Example 1-2

Preparation of a Pharmaceutical Composition Containing (R)-4-[(R)-3-amino-4-(2,4,5-trifluorophenyl)butanoyl]-3-(t-butoxymethyl)piperazin-2-one(tartrate) and Metformin at a Ratio of 5:1 Based on $ED_{30}$ Preparation was performed similarly to the method in Example 1-1 to have each composition (0.042~0.33 mg/kg of the compound prepared in Preparation Example 1: 1.25~10 mg/kg of metformin)/10 mL.

Example 1-3

Preparation of a Pharmaceutical Composition Containing (R)-4-[(R)-3-amino-4-(2,4,5-trifluorophenyl)butanoyl]-3-(t-butoxymethyl)piperazin-2-one(tartrate) and Metformin at a Ratio of 1:1 Based on $ED_{30}$ Preparation was performed similarly to the method in Example 1-1 to have each composition (0.025~0.2 mg/kg of the compound prepared in Preparation Example 1: 3.25~30 mg/kg of metformin)/10 mL.

Example 1-4

Preparation of a Pharmaceutical Composition Containing (R)-4-[(R)-3-amino-4-(2,4,5-trifluorophenyl)butanoyl]-3-(t-butoxymethyl)piperazin-2-one(tartrate) and Metformin at a Ratio of 1:3 Based on $ED_{30}$ Preparation was performed similarly to the method in Example 1-1 to have each composition (0.0125~0.1 mg/kg of the compound prepared in Preparation Example 1: 5.625~45 mg/kg of metformin)/10 mL.

Example 2

Preparation of a Mixed Composition of a Compound Represented by Formula 1 and Insulin Sensitizer

Example 2-1

Preparation of a Pharmaceutical Composition Containing (R)-4-[(R)-3-amino-4-(2,4,5-trifluorophenyl)butanoyl]-3-(t-butoxymethyl)piperazin-2-one(tartrate) and Rosiglitazone at a Ratio of 1:0.4 Based on Weight Ratio The compound prepared in Preparation Example 1 and rosiglitazone were weighed, and 0.5% methylcellulose was used to prepare 5 mL/kg of a suspension with each composition (1 mg of the compound prepared in Preparation Example 1+0.4 mg of rosiglitazone)/5 mL.

Example 2-2

Preparation of a Pharmaceutical Composition Containing (R)-4-[(R)-3-amino-4-(2,4,5-trifluorophenyl)butanoyl]-3-(t-butoxymethyl)piperazin-2-one(tartrate) and Rosiglitazone at a Ratio of 1:0.01 Based on Weight Ratio Preparation was performed similarly to the method in Example 2-1 to have each composition (40 mg of the compound prepared in Preparation Example 1+0.4 mg of rosiglitazone)/5 mL.

Example 3

Preparation of a Mixed Composition of a Compound Represented by Formula 1 and Insulin Secretagogue Example 3-1

Preparation of a Pharmaceutical Composition Containing (R)-4-[(R)-3-amino-4-(2,4,5-trifluorophenyl)butanoyl]-3-(t-butoxymethyl)piperazin-2-one(tartrate) and Glimepiride at a Ratio of 1:0.2 Based on Weight Ratio The compound prepared in Preparation Example 1 and glimepiride were weighed, and 0.5% methylcellulose was used to prepare 10 mL/kg of a suspension with each composition (0.1 mg of the compound prepared in Preparation Example 1+0.02 mg of glimepiride)/10 mL.

Example 3-2

Preparation of a Pharmaceutical Composition Containing (R)-4-[(R)-3-amino-4-(2,4,5-trifluorophenyl)butanoyl]-3-(t-butoxymethyl)piperazin-2-one(tartrate) and Glimepiride at a Ratio of 1:3.2 Based on Weight Ratio Preparation was performed similarly to the method in Example 3-1 to have each composition (0.1 mg of the compound prepared in Preparation Example 1+0.32 mg of rosiglitazone)/10 mL.

Example 4

Preparation of a Mixed Composition of a Compound Represented by Formula 1 and α-Glucosidase Inhibitor Example 4-1

Preparation of a Pharmaceutical Composition Containing (R)-4-[(R)-3-amino-4-(2,4,5-trifluorophenyl)butanoyl]-3-(t-butoxymethyl)piperazin-2-one(tartrate) and Voglibose at a Ratio of 1:0.03

The compound prepared in Preparation Example 1 and voglibose were weighed, and 0.5% methylcellulose was used to prepare 10 mL/kg of a suspension with each composition (0.3 mg of the compound prepared in Preparation Example 1+0.009 mg of voglibose)/10 mL.

Example 4

Preparation of a Pharmaceutical Composition Containing (R)-4-[(R)-3-amino-4-(2,4,5-trifluorophenyl)butanoyl]-3-(t-butoxymethyl)piperazin-2-one(tartrate) and Voglibose at a Ratio of 1:0.18

Preparation was performed similarly to the method in Example 4-1 to have each composition (0.3 mg of the compound prepared in Preparation Example 1+0.054 mg of voglibose)/10 mL.

Example 5

Preparation of a Mixed Composition of a Compound Represented by Formula 1 and Cannabinoid Receptor-1 Antagonist Example 5-1

Preparation of a Pharmaceutical Composition Containing (R)-4-[(R)-3-amino-4-(2,4,5-trifluorophenyl)butanoyl]-3-(t-butoxymethyl)piperazin-2-one(tartrate) and Rimonabant at a Ratio of 1:10 Based on Weight Ratio The compound prepared in Preparation Example 1 and rimonabant were weighed, and 0.5% methylcellulose was used to prepare 5 mL/kg of a suspension with each composition (0.3 mg of the compound prepared in Preparation Example 1+3 mg of rimonabant)/5 mL.

Example 5-2

Preparation of a Pharmaceutical Composition Containing (R)-4-[(R)-3-amino-4-(2,4,5-trifluorophenyl)butanoyl]-3-(t-butoxymethyl)piperazin-2-one(tartrate) and Rimonabant at a Ratio of 1:1 based on Weight Ratio Preparation was performed similarly to the method in Example 5-1 to have each composition (3 mg of the compound prepared in Preparation Example 1+3 mg of rimonabant)/5 mL.

Experimental Example 1

Measurement of Synergistic Effects of a Mixed Composition of a Compound Obtained in Preparation <1-1> Measurement of Synergistic Effects of a Mixed Composition of a Compound Prepared in Preparation Example 1 and Metformin by Single Administration in Normal Mice In order to examine synergistic effects of a mixed composition of a compound prepared in Preparation Example 1 of the present invention and metformin by single administration, the following experiment was performed on the individual materials and the mixed composition.

Experimental Subject and Experimental Method

Laboratory mice (C57BL/6 mice) as experimental subjects were fasted for 16 to 17 hours prior to the experiments. Blood was collected from caudal veins of mice in the morning on the day of the experiment and a blood glucose level was measured with an ACCU-CHEK ACTIVE Blood Glucose Meter (Roche Diagnostics). The pharmaceutical composition of the present invention was given orally 30 min prior to glucose administration (−30 min), followed by oral administration of a glucose solution (2 g/kg/10 mL) after 30 min (0 min). Blood collection was made at designated time points—just prior to drug administration, just prior to glucose administration, and 15, 30, 60 and 90 min after glucose administration.

Calculation of $ED_{30}$ of a Compound Prepared in Preparation Example 1 and Metformin Effects of single administration of the individual agents on a blood glucose change curve in an oral glucose tolerance test (OGTT) were identified by percent inhibition (%) and $ED_{30}$. The percent inhibition values for each treatment were generated from the area under curve (AUC) data normalized to the non-glucose challenged controls by subtracted blood glucose AUC of non-glucose challenged controls from glucose challenged groups, and comparing the value with that of a control group in which glucose has been administered. In general, it is suggested that an effective dose is defined as a dose to suppress the AUC by 30% or more in mouse experiments (WO2006/076231 A2). The $ED_{30}$ value refers to a dose at which 30% of the percent inhibition is exhibited, and was calculated by using a linear regression analysis at the third dose interval in the present Example.

As a result, it was identified that the $ED_{30}$ of a compound prepared in Preparation Example 1 of the present invention was 0.20 mg/kg and the $ED_{30}$ of metformin was 29.6 mg/kg (Table 1, Table 2).

TABLE 1

Results of glucose tolerance of a compound prepared in Preparation Example 1

| Single administration dose (mg/kg) | Percent inhibition (%) | $ED_{30}$ ± (SEM) |
|---|---|---|
| 0.1 | 18.5 | 0.20 ± 0.04 |
| 0.3 | 38.7 | |
| 1 | 54.8 | |

TABLE 2

Results of glucose tolerance of metformin

| Single administration dose (mg/kg) | Percent inhibition (%) | $ED_{30}$ ± (SEM) |
|---|---|---|
| 10 | 7.43 | 29.6 ± 6.68 |
| 30 | 29.06 | |
| 100 | 54.46 | |

Measurement of Degree of Synergistic Effects of a Mixed Compound of a Compound Prepared in Preparation Example 1 and Metformin (a Mixed Composition in Example 1)

Feasible synergistic effects of a composition at each fixed ratio were analyzed by isobologram (R. J. Tallarida et al, Life Sci. 1989, 45, 947). This process includes the decision of a dose of the mixture, at which the percent inhibition of 30% is exhibited ($ED_{30mix}$) in the OGTT experiment and the corresponding dose ($ED_{30add}$) expected under a simple additivity. When the result of $ED_{30mix}<ED_{30add}$ is established at a certain fixed ratio, the mixture has synergistic effects. $ED_{30add}$ was calculated from $ED_{30}$ of each drug. In FIG. 1, fractions of the $ED_{30}$ values of each material are present on each axis thereof. The $ED_{30}$ value of the compound prepared in Preparation Example 1 only is 0.2 mg/kg and shown as value 1 in FIG. 1, and the $ED_{30}$ value of metformin only is 30 mg/kg and shown as value 1 in FIG. 1. Therefore, the line combining the $ED_{30}$ values of the two individual drugs indicates a simple additivity ($ED_{30add}$) calculated from glucose tolerance effects at different ratios. Therefore, the points designated as A, B, C, and D in FIG. 1 with respect to each mixture studied indicate fractions of $ED_{30}$ values ($ED_{30mic}$) determined by actual experiments performed on a mixtures of the compound prepared in Preparation Example 1 and metformin at ratios of 9:1, 5:1, 1:1, and 1:3. The points A', B', C', and D' in FIG. 1 indicate fractions of doses ($ED_{30add}$) corresponding to mixtures of the compound prepared in Preparation Example 1 and metformin at ratios of 9:1, 5:1, 1:1, and 1:3 expected under a simple additivity.

The ratios of doses actually administered to animals in each fraction were calculated by multiplying 0.2 mg/kg and 30 mg/kg which are $ED_{30}$ values of the compound prepared in Preparation Example 1 and metformin, respectively with a desired ratio. Administrations were performed in the ranges of: 0.045~0.36 mg/kg of the compound prepared in Preparation Example 1+0.75~6 mg/kg of metformin at a ratio of 9:1, 0.042~0.33 mg/kg of the compound prepared in Preparation Example 1+1.25~10 mg/kg of metformin at a ratio of 5:1, 0.025~0.2 mg/kg of the compound prepared in Preparation Example 1+3.25~30 mg/kg of metformin at a ratio of 1:1, 0.0125~0.2 mg/kg of the compound prepared in Preparation Example 1+5.625~45 mg/kg of metformin at a ratio of 1:3. When this is applied to a healthy adult (about 70 kg), the dose corresponds to 0.88~25.2 mg of the compound prepared in Preparation Example 1 and 52.5~3150 mg of metformin, and includes a daily clinical dose of metformin, which is 500~2000 mg.

As a result of experiments, the $ED_{30mix}/ED_{30add}$ values of mixtures at ratios of 9:1, 5:1, 1:1, and 1:3 are 0.817, 0.437, 0.359, and 0.443, values calculated based on fractions of each ED30 value of the compound prepared in Preparation Example 1 and metformin (Table 3). From this result, $ED_{30mix}$ was calculated by multiplying the actual dose of $ED_{30add}$ corresponding to each ratio with $ED_{30mix}/ED_{30add}$, and it was identified that improvement effects in synergistic glucose tolerance were observed due to $ED_{30mix}<ED_{30add}$ at all the ratios. In particular, 2-fold or more improvement effects in glucose tolerance ($ED_{30add}/ED_{30mix}$) were observed in mixtures at ratios of 5:1, 1:1, and 1:3. The interactions of correct ratios selected based on fractions of $ED_{30}$ values of each material are shown in Table 3 and the isobologram of FIG. 1.

TABLE 3

Synergistic effects of a mixed composition of a compound prepared in Preparation Example 1 and metformin

| | Fraction of $ED_{30}$ value Compound of Preparation Example 1: metformin | $ED_{30mix}$ Compound of Preparation Example 1: metformin (mg/kg, p.o.) | $ED_{30add}$ Compound of Preparation Example 1: metformin (mg/kg, p.o.) | $ED_{30mix}/ED_{30add}$ |
|---|---|---|---|---|
| Example 1-1 | 9:1 | 0.147 + 2.45 (A) | 0.18 + 3 (A') | 0.817 |
| Example 1-2 | 5:1 | 0.073 + 2.19 (B) | 0.167 + 5 (B') | 0.437 |
| Example 1-3 | 1:1 | 0.036 + 5.38 (C) | 0.1 + 15 (C') | 0.359 |
| Example 1-4 | 1:3 | 0.022 + 9.96 (D) | 0.05 + 22.5 (D') | 0.443 |

( ) indicates a position on the isobologram in FIG. 1.

Figure 2:
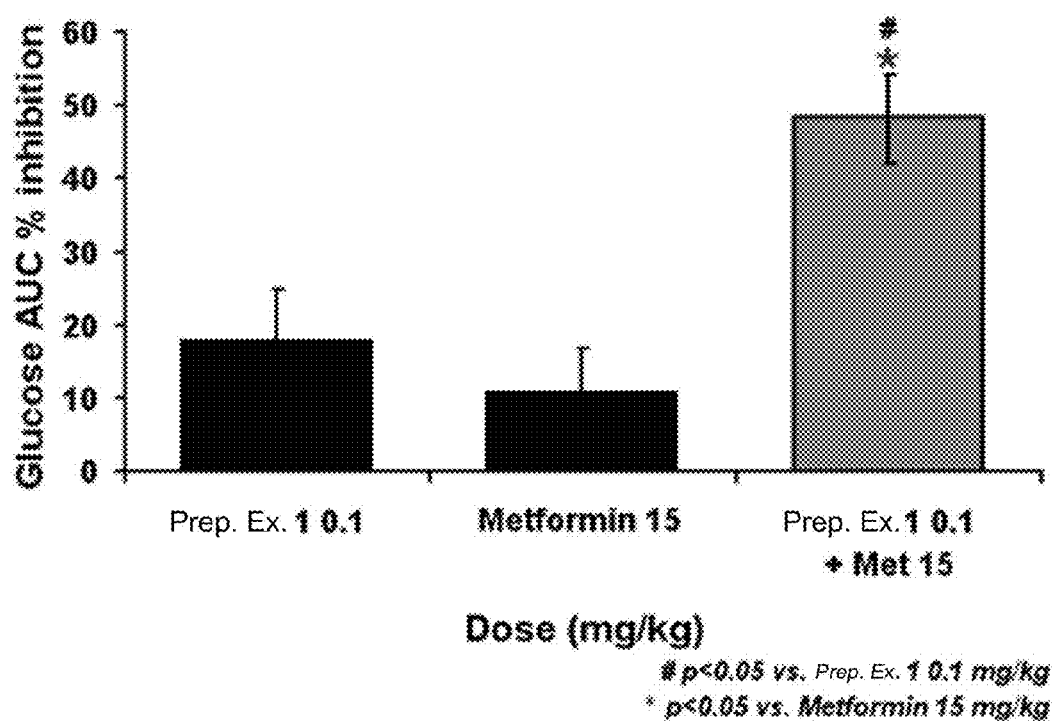
FIG. 2 is a graph showing the percent inhibition of the individual components only and a mixed composition of compound of Formula 1 and metaformin at various animal administration doses.

In addition, FIG. 2 shows that the mixed composition exhibited significant improvement effects in glucose tolerance, compared to the percent inhibition of each material administered alone.

As a result, when the ratio is converted into a ratio of doses of a compound prepared in Preparation Example 1 and metformin actually administered to animals, improvement effects in glucose tolerance were observed over the wide dose range of 1:16.7 to 1:450.

<1-2> Measurement of Synergistic Effects of a Mixed Composition of a Compound Prepared in Preparation Example 1 and Metformin by Single Administration and by Repeated Administration in Obese Mice -Experimental Subject and Experimental Method- In order to examine synergistic effects of a compound prepared in Preparation Example 1 of the present invention and metformin complex by repeated administration, effects of a single administration to obese mice on an OGTT blood glucose change curve and of a 2-week repeated administration on the percent inhibition of blood glucose were evaluated. Diet-induced obesity mice obtained by supplying experimental mice (C57BL/6 mice) with high fat fodder (60 kcal % fat, Research Diets, D12492) for 5 month were used as experimental subjects. 0.5% methylcellulose (MC) was used to prepare a suspension of the compound 1 prepared in Preparation Example 1 with a composition of 0.1 mg/kg and 0.15 mg/kg. 0.5% MC was used to prepare a suspension of metformin with a composition of 7.5 mg/kg and 15 mg/kg. 6 mL/kg of the complex was prepared in doses of (0.1 mg/kg of a compound prepared in Preparation Example 1+15 mg/kg of metformin)/5 mL and (0.15 mg/kg of a compound prepared in Preparation Example 1+7.5 mg/kg of metformin)/5 mL.

Obese mice were fasted for 16 to 17 hours prior to the experiments, blood was collected from caudal veins of mice in the morning on the day of the experiment and a blood glucose level was measured with an ACCU-CHEK ACTIVE Blood Glucose Meter (Roche Diagnostics). The mixed composition of the present invention was given orally 30 min prior to glucose administration (−30 min), followed by oral administration of a glucose solution (2 g/kg/10 mL) after 30 min (0 min). Blood collection was made at designated time points—just prior to drug administration, just prior to glucose administration, and 15, 30, 60 and 90 min after glucose administration. The percent inhibition value was calculated by calculating an area under curve of each group and comparing the value with that of a control group in which glucose had been administered.

Figure 3:
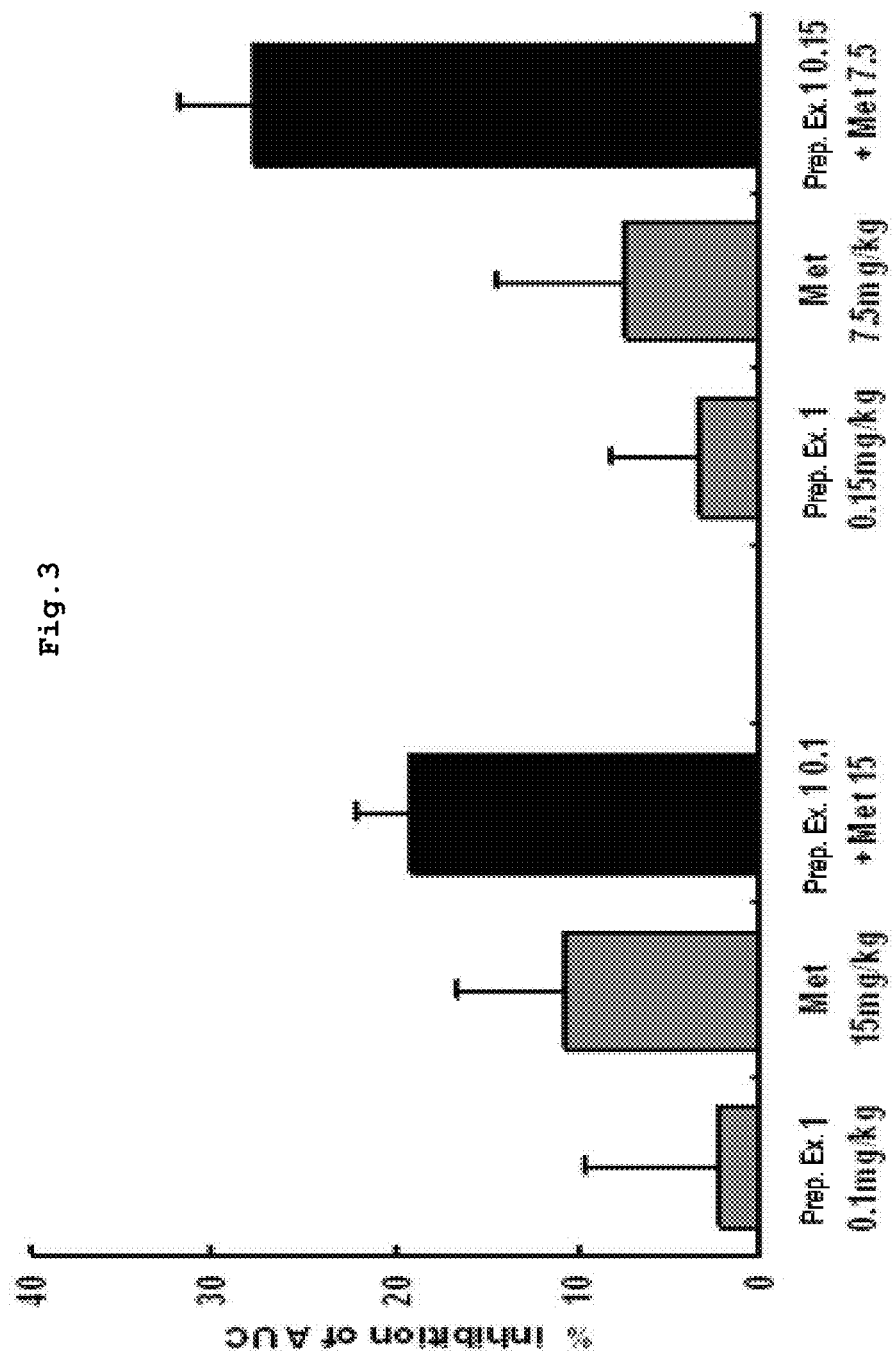
FIG. 3 is a graph showing the percent inhibition in terms of improvement in glucose tolerance of a single dose compound 1, metformin, and a mixed composition at various animal administration dose ratios of 1:50 to 1:150 in obese mice.

-Measurement of Synergistic Effects by a Single Administration of a Mixed Composition- The percent inhibition by a single administration of each administered drug was shown in the following Table 4, Table 5, and FIG. 3.

TABLE 4

Percent inhibition of a compound prepared in Preparation Example 1 and metformin

| Administered drug and administered dose (mg/kg) | Percent inhibition (%) |
|---|---|
| Compound prepared in Preparation Example 1 0.1 | 2 |
| Compound prepared in Preparation Example 1 0.15 | 3 |
| Metformin 7.5 | 7 |
| Metformin 15 | 11 |

TABLE 5

Percent inhibition of a mixed composition of a compound prepared in Preparation Example 1 and metformin

| | Administered drug and administered dose (mg/kg) | Percent inhibition (%) |
|---|---|---|
| Example 1-2 | Compound prepared in Preparation Example 1 0.1 + Metformin 15 | 19 |
| Example 1-3 | Compound prepared in Preparation Example 1 0.15 + Metformin 7.5 | 28 |

For improvement in blood glucose AUC, 2% and 3% percent inhibitions were exhibited by a compound prepared in Preparation Example 1 at 0.1 mg/kg and 0.15 mg/kg, while 7% and 11% percent inhibitions were exhibited by metformin at 7.5 mg/kg and 15 mg/kg. On the contrary, blood glucose AUCs of complexes of a compound prepared in Preparation Example 1 at 0.1 mg/kg+metformin at 15 mg/kg and a compound prepared in Preparation Example 1 at 0.15 mg/kg+metformin at 7.5 mg/kg were inhibited by 19% and 28%, respectively. This indicates that synergistic effects higher than the arithmetic sum of single administrations of individual drugs were observed (FIG. 3).

-Synergistic Effects by Repeated Administration-

Figure 4:
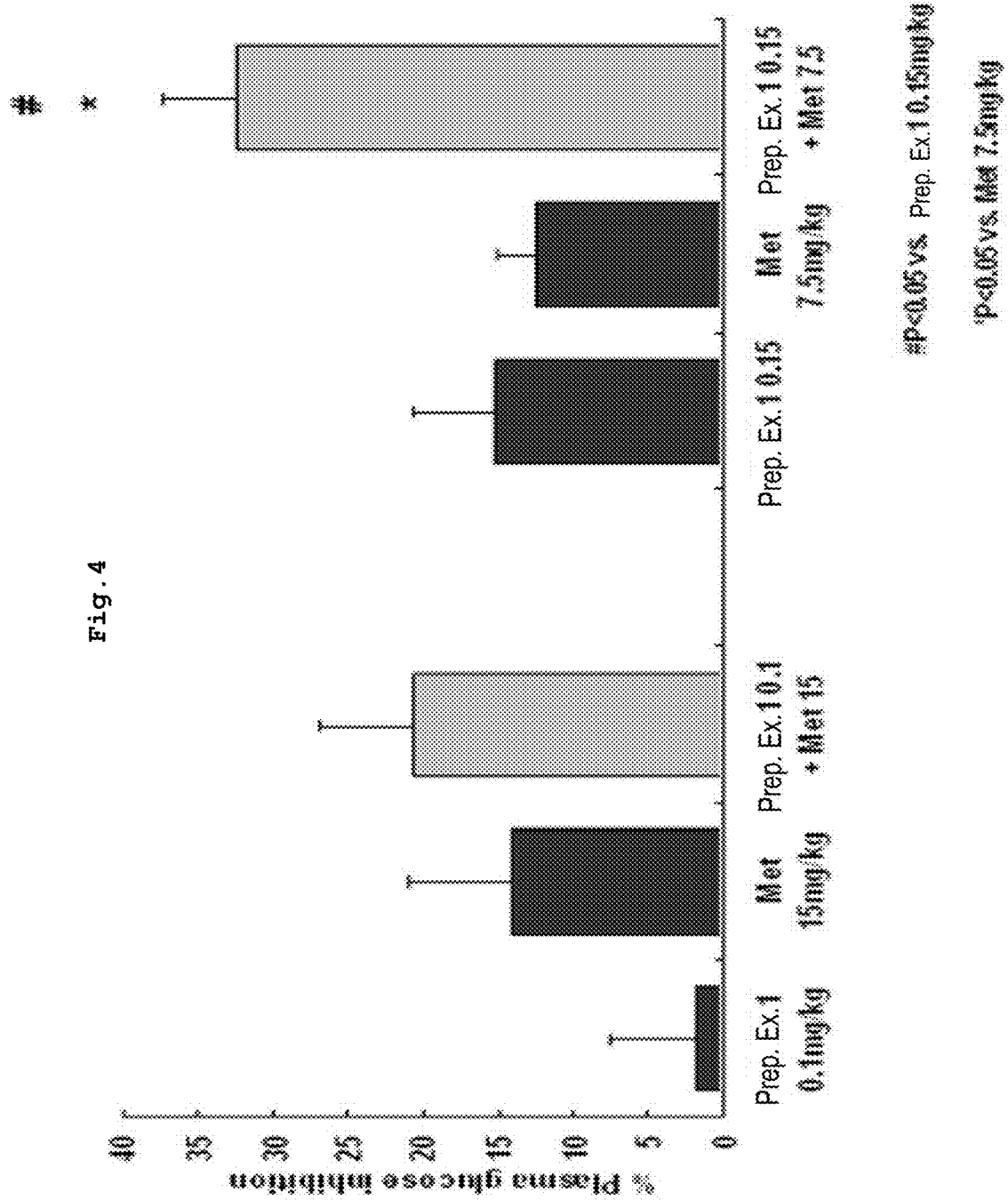
FIG. 4 is a graph showing the percent inhibition in terms of plasma glucose of a compound 1, metformin, and a mixed composition by administration at various animal administration dose ratios of 1:50 to 1:150 for two weeks in obese mice.

The percent inhibition by repeated administration 2 weeks after administration is shown in Table 6, Table 7, and FIG. 4.

TABLE 6

Percent inhibition by administration of a compound prepared in Preparation Example 1 and metformin

| Administered drug and administered dose (mg/kg) | Percent inhibition (%) |
|---|---|
| Compound prepared in Preparation Example 1 0.1 | 2 |
| Compound prepared in Preparation Example 1 0.15 | 15 |
| Metformin 7.5 | 13 |
| Metformin 15 | 14 |

TABLE 7

Percent inhibition of a mixed composition of a compound prepared in Preparation Example 1 and metformin

| | Administered drug and administered dose (mg/kg) | Percent inhibition (%) |
|---|---|---|
| Example 1-2 | Compound prepared in Preparation Example 1 0.1 + Metformin 15 | 21 |
| Example 1-3 | Compound prepared in Preparation Example 1 0.15 + Metformin 7.5 | 31 |

Plasma glucose by administration of a compound prepared in Preparation Example 1 at 0.1 and 0.15 mg/kg was improved by 2% and 15%, compared to a control group. Metformin at 7.5 and 15 mg/kg improved plasma glucose by 13% and 14%, compared to a level of a control group. On the contrary, complexes of a compound prepared in Preparation Example 1 at 0.1 mg/kg+metformin at 15 mg/kg or a compound prepared in Preparation Example 1 at 0.15 mg/kg+metformin at 7.5 mg/kg improved plasma glucose by 21% and 31%, respectively. This indicates that synergistic effects higher than the arithmetic sum of single administrations of individual drugs were observed (FIG. 4).

As a result, when the ratio is converted into a ratio of doses of a compound prepared in Preparation Example 1 and metformin actually administered to animals during a repeated administration, improvement effects in synergistic efficacies were observed over the wide dose range of 1:50 to 1:150.

Experimental Example 2

Measurement of Synergistic Effects By Administration of a Mixed Composition of a Compound of Formula 1 and Insulin Sensitizer to Obese Mice 2-1> Measurement of Synergistic Effects by Repeated Administration of a Mixed Composition of a Compound Prepared in Preparation Example 1 and Rosiglitazone to Obese Mice -Experimental Subject and Experimental Method- In order to examine synergistic effects of a complex by a compound prepared in Preparation Example 1 of the present invention and an insulin sensitizer PPARγ agonist, the percent inhibition of blood glucose by repeated administration of the complex to db/db mice as diabetic mice was evaluated. Eight-week-old male mice (db/db mice) were used as experimental subjects. It is known that rosiglitazone is a TZD-series drug which has the same parent nucleus as pioglitazone which is currently used in clinical practice and regulates blood glucose through the same mechanism, and the dose in the present evaluation was selected as 0.4 mg/kg in consideration of an essential ratio of clinical dose based on $ED_{30}$ with respect to blood glucose lowering in a diabetic mouse experiment. The dose of a compound prepared in Preparation Example 1 with respect to rosiglitazone at a fixed dose was selected at 1 mg/kg and 40 mg/kg (complex ratio 1:0.01~1:0.4) in consideration of a complex ratio in an expected clinical dose. Since the complex ratio of 1:0.01 or less to 1:0.4 or more is a value deviating from a daily clinical dose of rosiglitazone and there is concern about the possibility of poor efficacy or adverse side effects, the complex ratio was limited to 1:0.01~1:0.4. 0.5% methylcellulose (MC) was at each drug concentration to prepare suspensions. Each compound was weighed, and 0.5% methylcellulose was used to prepare 5 mL/kg of suspensions with each composition of (1 mg of the compound prepared in Preparation Example 1+0.4 mg of rosiglitazone)/5 mL and (40 mg of the compound prepared in Preparation Example 1+0.4 mg of rosiglitazone)/5 mL.

The drug was orally given to diabetic mice and blood was collected from caudal veins of the mice after 1 hour of the administration to measure the blood glucose with an ACCU-CHEK ACTIVE Blood Glucose Meter (Roche Diagnostics). The percent inhibition value with respect to blood glucose was calculated by comparison with a control group.

-Measurement of Synergistic Effects by Administration-

Figure 5:
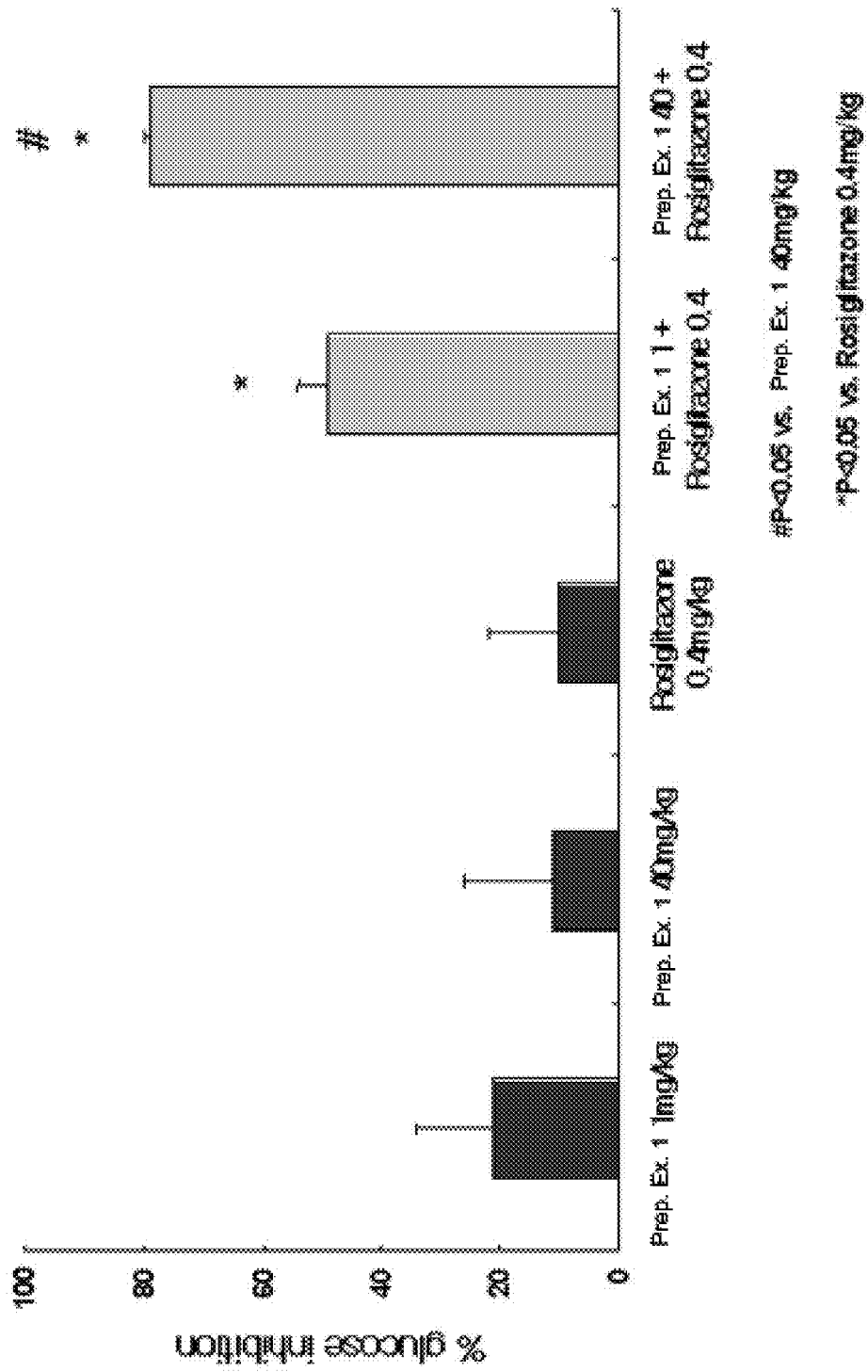
FIG. 5 is a graph showing the percent inhibition in terms of blood glucose of a compound 1, a PPARγ agonist, and a mixed composition by administration at various animal administration dose ratios of 1:0.01 to 1:0.4 for seven days in diabetic mice.

Experimental results about the percent inhibition of blood glucose in comparison with a control group by administration of the drug for 7 days are shown in the following Table 8, Table 9, and FIG. 5.

TABLE 8

Percent inhibition during administration of a compound prepared in Preparation Example 1 and rosiglitazone

| Administered drug and administered dose (mg/kg) | Percent inhibition (%) |
|---|---|
| Compound prepared in Preparation Example 1 1 | 21 |
| Compound prepared in Preparation Example 1 40 | 11 |
| Rosiglitazone 0.4 | 10 |

TABLE 9

Percent inhibition during administration of a mixed composition of a compound prepared in Preparation Example 1 and rosiglitazone

| | Administered drug and administered dose (mg/kg) | Percent inhibition (%) |
|---|---|---|
| Example 2-1 | Compound prepared in Preparation Example 1 1 + Rosiglitazone 0.4 | 49 |
| Example 2-2 | Compound prepared in Preparation Example 1 40 + Rosiglitazone 0.4 | 79 |

The percent inhibitions of blood glucose by administration of a compound prepared in Preparation Example 1 at 1 mg/kg and 40 mg/kg compared to a control group was calculated as 21% and 11%, respectively, and 10% improvement was made by administration of a PPARγ agonist rosiglitazone at 0.4 mg/kg. In addition, improvements in complexes of a compound prepared in Preparation Example 1 at 1 mg/kg+rosiglitazone at 0.4 mg/kg or a compound prepared in Preparation Example 1 at 40 mg/kg+rosiglitazone at 0.4 mg/kg were calculated as 49% and 79%, respectively. This indicates that synergistic effects higher than the arithmetic sum of single administrations of individual drugs were observed (FIG. 5).

As a result, when the ratio is converted into a ratio of doses of a compound prepared in Preparation Example 1 and a PPARγ agonist rosiglitazone actually administered to diabetic mice, improvement effects in synergistic efficacies were observed over the dose range of 1:0.01 to 1:0.4.

Experimental Example 3

Measurement of Synergistic Effects of a Mixed Composition of a Compound Prepared in Preparation Example 1 and Insulin Secretagogue <3-1> Measurement of Synergistic Effects of a Mixed Composition of a Compound Prepared in Preparation Example 1 and Glimepiride by Single Administration -Experimental Subject and Experimental Method- In order to examine synergistic effects of a complex of a compound prepared in Preparation Example 1 of the present invention and an insulin secretagogue sulfonyl urea-series drug, the percent inhibitions of single administration OGTT blood glucose change curves by individual materials and complexes were evaluated. 8-week-old male experimental mice (C57BL/6 mice) were used and fasted for 16 to 17 hours prior to the experiments. Blood was collected from caudal veins of mice in the morning on the day of the experiment and a blood glucose level was measured with an ACCU-CHEK ACTIVE Blood Glucose Meter (Roche Diagnostics). The mixed composition of the present invention was given orally 30 min prior to glucose administration (−30 min), followed by oral administration of a glucose solution (2 g/kg/10 mL)

after 30 min (0 min). Blood collection was made at designated time points—just prior to drug administration, just prior to glucose administration, and 15, 30, 60 and 90 min after glucose administration. The percent inhibition value was calculated by calculating an area under curve of each group, except for a group in which glucose had not been administered, and comparing the value with that of a control group in which glucose had been administered. In order to evaluate synergistic or additive effects by complex in the present evaluation, 0.5% methylcellulose (MC) was used to prepare a suspension with a dose of a compound prepared in Preparation Example 1 at 0.1 mg/kg, and 0.5% MC was also used to prepare a suspension with a composition of an insulin secretagogue sulfonyl urea-series drug and glimepiride at 0.02 mg/kg and 0.32 mg/kg such that a complex ratio may be included at a clinical dose expected in a fixed state of a compound prepared in Preparation Example 1. Glimepiride is a drug which promotes the secretion of insulin from pancreas with the same mechanism as glipizide, glybenclamide, and the like. A complex thereof was prepared at 10 mL per kg by weighing individual compounds and mixing the compounds with each composition ((a compound prepared in Preparation Example 10.1 mg+glimepiride 0.02 mg)/10 mL and (a compound prepared in Preparation Example 10.1 mg+glimepiride 0.32 mg)/10 mL)). When the mixing ratio is 1:0.2 or less, or 1:3.2 or more, poor efficacy or adverse side effects may occur. Thus, the mixing ratio of a compound prepared in Preparation Example 1 and glimepiride was set at 1:0.2~1:3.2.

-Measurement of Synergistic Effects by Administration-

Figure 6:
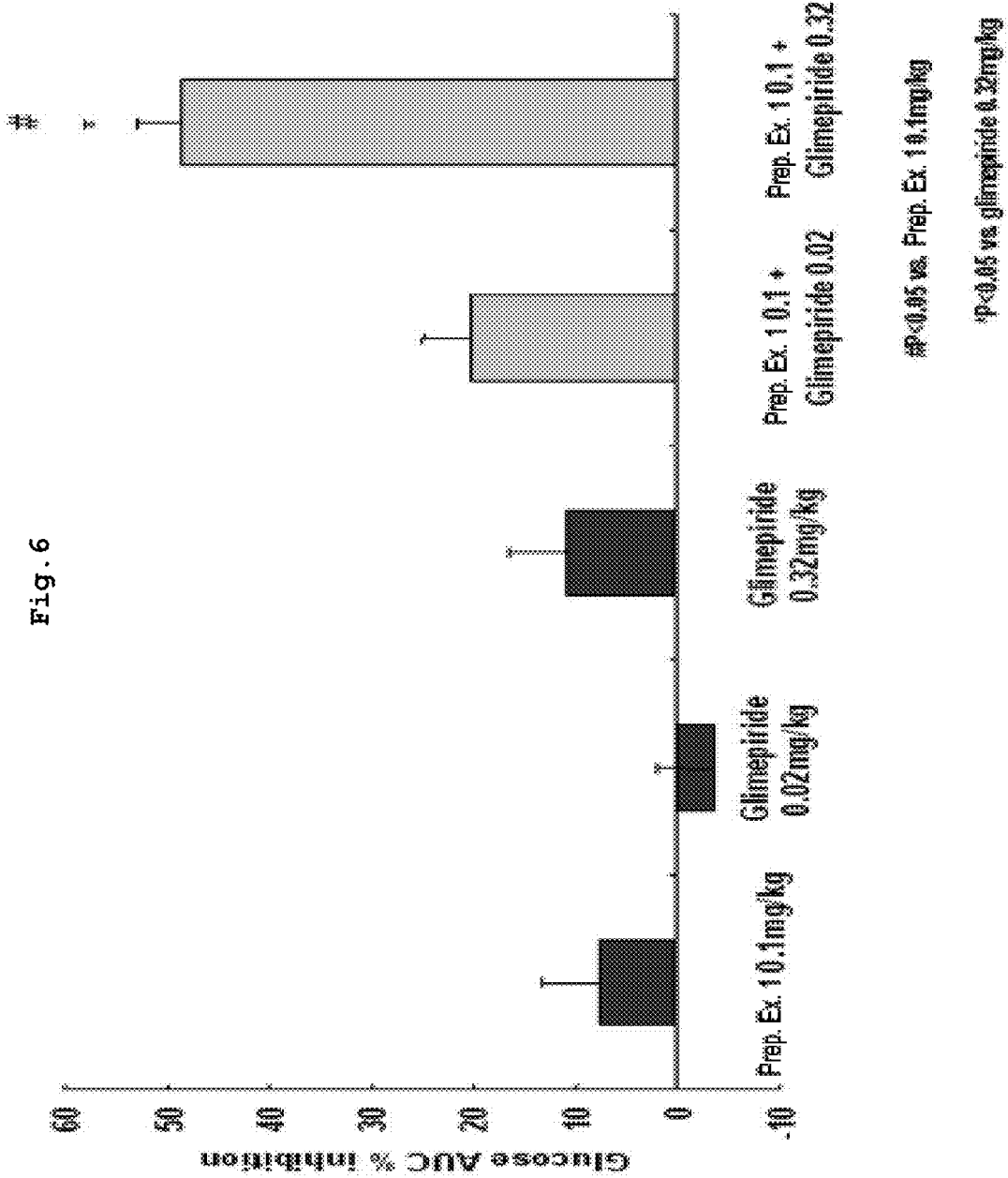
FIG. 6 is a graph showing the percent inhibition in terms of improvement in glucose tolerance of a compound 1, a sulfonyl urea-series agent, and a mixed composition by administration at various dose ratios of 1:0.2 to 1:3.2.

Experimental results of the percent inhibition of blood glucose in comparison with a control group in experiments are shown in the following Table 10, Table 11, and FIG. 6.

TABLE 10

Percent inhibition by administration of a compound prepared in Preparation Example 1 and glimepiride

| Administered drug and administered dose (mg/kg) | Percent inhibition (%) |
|---|---|
| Compound prepared in Preparation Example 1 0.1 | 7.7 |
| Glimepiride 0.02 | −3.69 |
| Glimepiride 0.32 | 10.9 |

TABLE 11

Percent inhibition by administration of a mixed composition of a compound prepared in Preparation Example 1 and glimepiride

| | Administered drug and administered dose (mg/kg) | Percent inhibition (%) |
|---|---|---|
| Example 3-1 | A compound prepared in Preparation Example 1 0.1 + Glimepiride 0.02 | 20.2 |
| Example 3-2 | A compound prepared in Preparation Example 1 0.1 + Glimepiride 0.32 | 48.7 |

As a result of the experiment, 7.7% of percent inhibition was exhibited in the case of a compound 1 prepared in Preparation Example 1 at 0.1 mg/kg in comparison with a control group. When glimepiride was used at 0.02 mg/kg and 0.32 mg/kg, the percent inhibition of blood glucose was calculated at −3.69% and 10.9%, respectively, compared to a control group. In addition, when complexes of a compound prepared in Preparation Example 1 at 0.1 mg/kg+glimepiride at 0.02 mg/kg and a compound prepared in Preparation Example 1 at 0.1 mg/kg+glimepiride at 0.32 mg/kg were used, the percent inhibition was calculated as 20.2% and 48.7%, respectively. This indicates that synergistic effects higher than the arithmetic sum of single administrations of individual drugs were observed (FIG. 6).

In summary, improvements in synergistic effects were observed over the dose ratio of 1:0.2 to 1:3.2 of a compound prepared in Preparation Example 1 and glimepiride.

Experimental Example 4

Measurement of Synergistic Effects of a Mixed Composition of a Compound of Formula 1 and α-Glucosidase Inhibitor <4-1> Measurement of Synergistic Effects by Administration of a Mixed Composition of a Compound Prepared in Preparation Example 1 and Voglibose -Experimental Subject and Experimental Method- In order to examine synergistic effects of a compound prepared in Preparation Example 1 of the present invention and an α-glucosidase inhibitor-series drug by complexing drugs, the percent inhibition in a single administration oral sucrose tolerance test blood glucose change curve by individual materials and a complex thereof was evaluated. 8-week-old male experimental mice (C57BL/6 mice) were used as experimental subjects. The mice were fasted for 16 to 17 hours prior to the experiments. Blood was collected from caudal veins of mice in the morning on the day of the experiment and a blood glucose level was measured with an ACCU-CHEK ACTIVE Blood Glucose Meter (Roche Diagnostics). The pharmaceutically mixed composition of the present invention was given orally 30 min prior to sucrose administration (−30 min), followed by oral administration of a glucose solution (2 g/kg/10 mL) after 30 min (0 min). Blood collection was made at designated time points—just prior to drug administration, just prior to sucrose administration, and 15, 30, 60, 90, and 120 min after sucrose administration. The percent inhibition value was calculated by calculating an area under curve of each group, except for sucrose had not been administered, and comparing the value with that of a control group in which sucrose had been administered. In order to evaluate synergistic or additive effects by complexes in the present evaluation, 0.5% methylcellulose (MC) was used to prepare a suspension with a compound prepared in Preparation Example 1 at a dose of 0.3 mg/kg, and 0.5% MC was also used to prepare a suspension with a composition of an α-glucosidase inhibitor and voglibose at 0.009 mg/kg and 0.054 mg/kg (complex ratio 1:0.031:0.18) such that a complex ratio may be included at a clinical dose expected in a state where a dose of a compound prepared in Preparation Example 1 was fixed. Voglibose is a drug with the same mechanism as acarbose, and individual drugs were weighed to have a composition ((a compound prepared in Preparation Example 10.3 mg+voglibose 0.009 mg)/10 mL and (a compound prepared in Preparation Example 10.3 mg+voglibose 0.054 mg)/10 mL and prepare 10 mL per kg of a suspension. When the mixing ratio is 1:0.03 or less, or 1:0.18 or more, poor efficacy or adverse side effects may occur. Thus, the mixing ratio was set at 1:0.03~1:0.18.

-Synergistic Effects by Administration-

Figure 7:
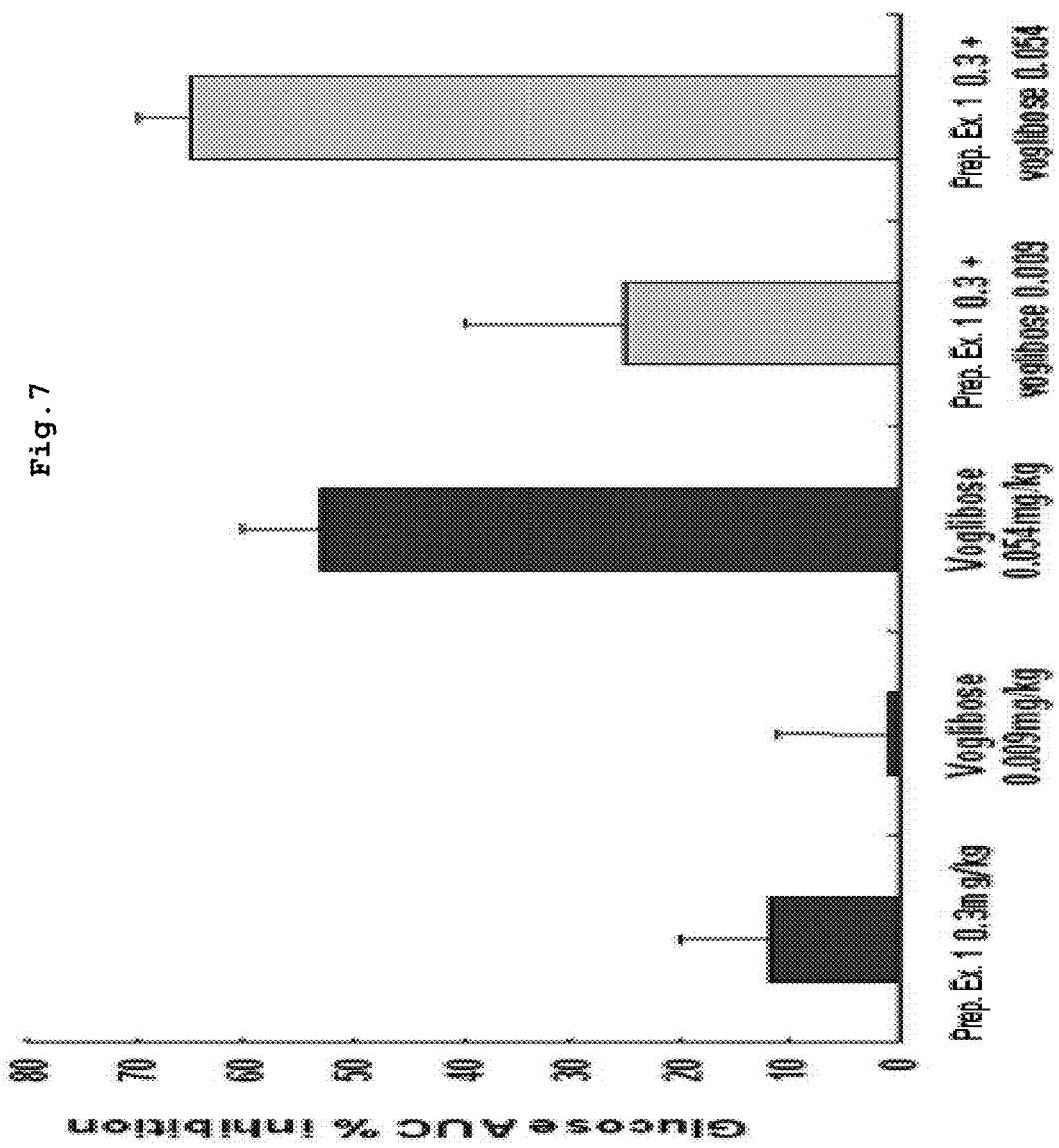
FIG. 7 is a graph showing the percent inhibition in terms of improvement in glucose tolerance of a compound 1, an α-glucosidase inhibitor, and a mixed composition by administration at various dose ratios of 1:0.03 to 1:0.18.

Experimental results of the percent inhibition of blood glucose in comparison with a control group in experiments are shown in Table 12, Table 13, and FIG. 7.

TABLE 12

Percent inhibition during administration of a compound prepared in Preparation Example 1 and voglibose

| Administered drug and administered dose (mg/kg) | Percent inhibition (%) |
|---|---|
| A compound prepared in Preparation Example 1 0.3 | 12 |
| Voglibose 0.009 | 1 |
| Voglibose 0.054 | 53 |

TABLE 13

Percent inhibition during administration of a mixed composition of a compound prepared in Preparation Example 1 and voglibose

| | Administered drug and administered dose (mg/kg) | Percent inhibition (%) |
|---|---|---|
| Example 4-1 | A compound prepared in Preparation Example 1 0.3 + Voglibose 0.009 | 25 |
| Example 4-2 | A compound prepared in Preparation Example 1 0.3 + Voglibose 0.054 | 65 |

As a result of the experiment, 12% of percent inhibition was exhibited in the case of a compound 1 prepared in Preparation Example 1 at 0.3 mg/kg in comparison with a control group. When voglibose was used at 0.009 mg/kg and 0.054 mg/kg, the percent inhibition of blood glucose was calculated at 1% and 53%, respectively, compared to a control group. In addition, when complexes of a compound prepared in Preparation Example 1 at 0.3 mg/kg+voglibose at 0.009 mg/kg and a compound prepared in Preparation Example 1 at 0.3 mg/kg+voglibose at 0.054 mg/kg were used, the percent inhibition was calculated as 25% and 65.7%, respectively. This indicates that synergistic or additive effects higher than the arithmetic sum of single administrations of individual drugs were observed (FIG. 7).

In summary, improvements in synergistic or additive effects were observed over the wide dose ratio of 1:0.03 to 1:0.18 of a compound prepared in Preparation Example 1 and voglibose.

Experimental Example 5

Measurement of Synergistic Effects of a Mixed Composition of a Compound of Formula 1 and Cannabinoid Receptor-1 Antagonist <5-1> Synergistic Effects of a Mixed Composition of a Compound Prepared in Preparation Example 1 and Rimonabant with Respect to an OGTT Blood Glucose Change Curve by Repeated Administration -Experimental Subject and Experimental Method- In order to examine synergistic effects by repeated administration of a compound prepared in Preparation Example 1 and cannabinoid receptor-1 antagonist, effects of 4-week administration to obese mice on an OGTT blood glucose change curve and on fat mass were evaluated. Diet-induced obesity mice obtained by supplying experimental mice (C57BL/6 mice) with high fat fodder (60 kcal % fat, Research Diets, D12492) for 5 month were used as experimental subjects. 0.5% methylcellulose (MC) was used to prepare a suspension of the compound 1 prepared in Preparation Example 1 with a composition of 0.3 mg/kg which is presumed to be a dose of minimum effective efficacy and 3 mg/kg. 0.5% MC was used to prepare a suspension of rimonabant, a cannabinoid receptor-1 antagonist with a composition of 3 mg/kg. Rimonabant has the same parent nucleus structure as a cannabinoid receptor-1 antagonist, such as Otenabant, Ibinabant, and Surinabant, and 5 mL/kg of the complex thereof was prepared in doses of (0.3 mg of a compound prepared in Preparation Example 1+3 mg of rimonabant)/5 mL and (3 mg of a compound prepared in Preparation Example 1+3 mg/kg of rimonabant)/5 mL. When the mixing ratio is 1:0.1 or less, or 1:1 or more, the dose may exceed a daily clinical dose of rimonabant or poor efficacy may occur. Thus, the mixing ratio was set at 1:11:10.

Obese mice were fasted for 16 to 17 hours prior to the experiments, blood was collected from caudal veins of mice in the morning on the day of the experiment and a blood glucose level was measured with an ACCU-CHEK ACTIVE Blood Glucose Meter (Roche Diagnostics). The pharmaceutically mixed composition of the present invention was given orally 30 min prior to glucose administration (−30 min), followed by oral administration of a glucose solution (2 g/kg/10 mL) after 30 min (0 min). Blood collection was made at designated time points—just prior to drug administration, just prior to glucose administration, and 15, 30, 60, 90, and 120 min after glucose administration. The percent inhibition value was calculated by calculating an area under curve of each group and comparing the value with that of a control group in which glucose had been administered.

-Synergistic Effects by Administration-

Figure 8:
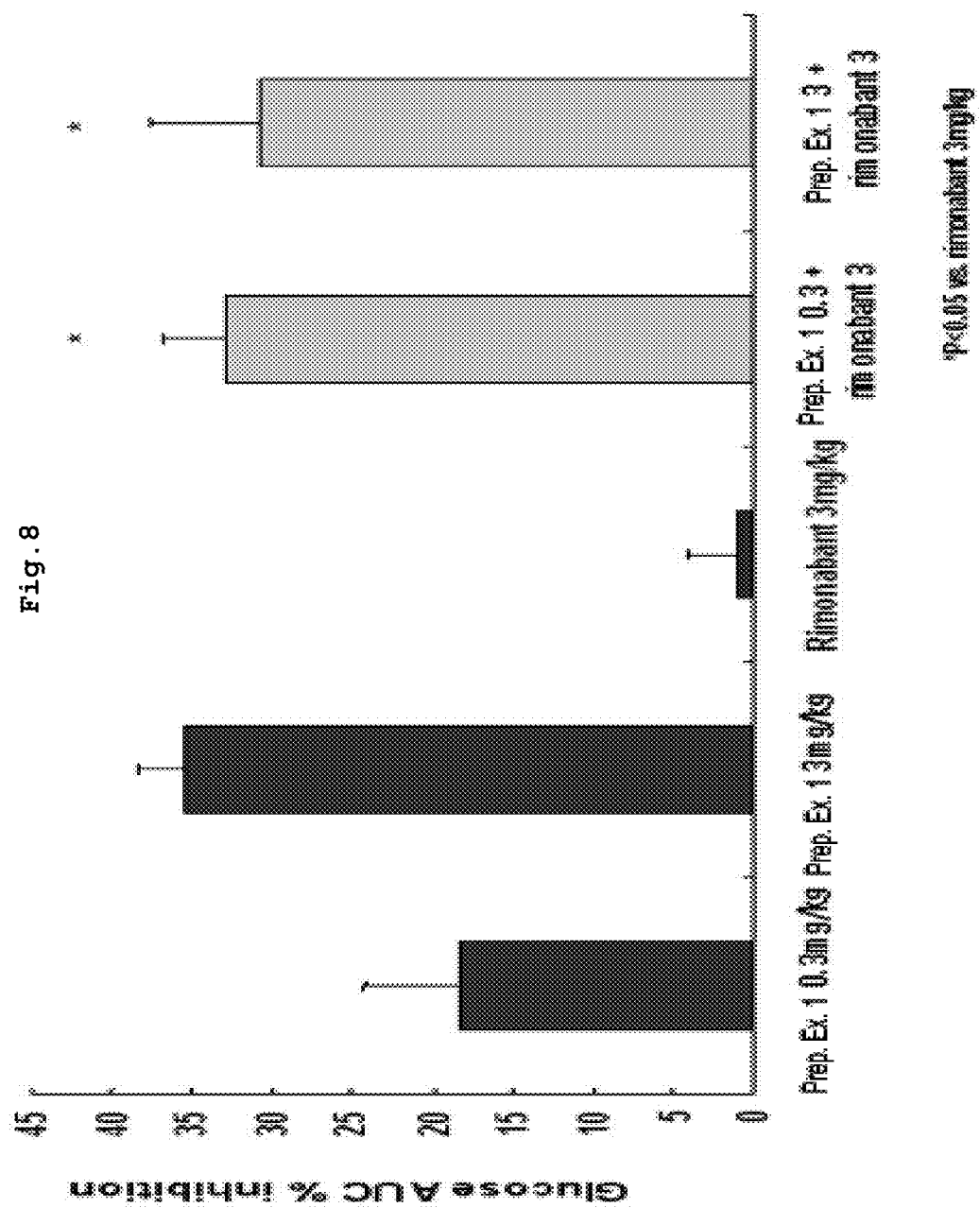
FIG. 8 is a graph showing the percent inhibition in terms of improvement in glucose tolerance of a compound 1, a cannabinoid receptor-1 antagonist, a mixed composition by administration at various dose ratios of 1:1 to 1:10.

Experimental results of the percent inhibition of blood glucose in comparison with a control group in experiments are shown in Table 14, Table 15, and FIG. 8.

TABLE 14

Percent inhibition of a compound prepared in Preparation Example 1 and rimonabant by administration

| Administered drug and administered dose (mg/kg) | Percent inhibition (%) |
|---|---|
| A compound prepared in Preparation Example 1 0.3 | 18.2 |
| A compound prepared in Preparation Example 1 3 | 35.3 |
| Rimonabant 3 | 1.1 |

TABLE 15

Percent inhibition of a mixed composition of a compound prepared in Preparation Example 1 and rimonabant by administration

| | Administered drug and administered dose (mg/kg) | Percent inhibition (%) |
|---|---|---|
| Example 5-1 | A compound prepared in Preparation Example 1 0.3 + Rimonabant 3 | 32.8 |
| Example 5-2 | A compound prepared in Preparation Example 1 3 + Rimonabant 3 | 30.7 |

The blood AUC by 0.3 mg/kg and 3 mg/kg of a compound prepared in Preparation Example 1 was inhibited by 18.2% and 35.3% compared to a control group. The blood AUC by 3 mg/kg of rimonabant was inhibited by 1.1%, compared to a control group. On the contrary, the blood AUC by 0.3 mg/kg of a compound prepared in Preparation Example 1+3 mg/kg of rimonabant or 3 mg/kg of a compound prepared in Preparation Example 1+3 mg/kg of rimonabant was inhibited by 32.8% and 30.7%, respectively. Thus, synergistic or additive effects were observed (FIG. 8).

<5-2> Effects of Fat Mass Reduction by Repeated Administration of a Mixed Composition of a Compound Prepared in Preparation Example 1 and Rimonabant -Experimental Subject and Experimental Method- Experiments were performed on the experimental subject and experimental drug in the same manner as in Experimental Example 5-1, the fat mass was calculated as a sum of epidydimal fat and retroperitoneal fat, and fat mass 4 weeks after administration was measured.

The results are shown in the following Tables 16 and 17.

TABLE 16

Effects of a compound prepared in Preparation Example 1 and rimonabant on fat mass reduction

| Experimental group | Fat mass (g) | % reduction |
|---|---|---|
| HF-DIO control group | 3.61 ± 0.20 | — |
| A compound prepared in Preparation Example 1 0.3 mg/kg | 3.67 ± 0.12 | −1.65 |
| A compound prepared in Preparation Example 1 3 mg/kg | 3.29 ± 0.21 | 8.71 |
| Rimonabant 3 mg/kg | 2.11 ± 0.31* | 41.5 |

*$P > 0.05$ vs. HF-DIO control group

TABLE 17

Effects of a compound prepared in Preparation Example 1 and rimonabant on fat mass reduction

| | Experimental group | Fat mass (g) | % reduction |
|---|---|---|---|
| Example 5-1 | A compound prepared in Preparation Example 1 0.3 mg/kg + Rimonabant 3 mg/kg | 2.09 ± 0.32* | 42.1 |
| Example 5-2 | A compound prepared in Preparation Example 1 3 mg/kg + Rimonabant 3 mg/kg | 1.76 ± 0.35* | 51.2 |

*$P > 0.05$ vs. HF-DIO control group

After 4 weeks of administration, fat mass by administration of a compound prepared in Preparation Example 1 at 0.3 mg/kg or 3 mg/kg was reduced by −1.65% and 8.71%, respectively, while fat mass by administration of a cannabinoid receptor-1 antagonist at 3 mg/kg was reduced by 41.5%. In addition, fat mass by administration of a compound prepared in Preparation Example 1 at 0.3 mg/kg+a cannabinoid receptor-1 antagonist at 3 mg/kg or a compound prepared in Preparation Example 1 at 3 mg/kg+a cannabinoid receptor-1 antagonist at 3 mg/kg was reduced by 42.1% and 51.2%, respectively. Thus, additive effects were observed.

Consequently, synergistic or additive efficacy improvement effects of a compound prepared in Preparation Example 1 and a cannabinoid receptor-1 antagonist were observed on obese mice over the dose ratio of 1:1 to 1:10.

Formulation Example

Preparation of a Pharmaceutical Preparation

| <1-1> Preparation of powder | |
|---|---|
| A mixed composition of a compound prepared in Preparation Example 1 and metformin | 2 g |
| Lactose | 1 g |

The above ingredients are mixed and filled in an airtight pouch to prepare a powder formulation.

| <1-2> Preparation of tablet formulation | |
|---|---|
| A mixed composition of a compound prepared in Preparation Example 1 and metformin | 100 mg |
| Cornstarch | 100 mg |
| Lactose | 100 mg |
| Magnesium stearate | 2 mg |

The above ingredients are mixed and then tabletted according to a conventional preparation method to prepare a tablet formulation.

| <1-3> Preparation of capsule formulation | |
|---|---|
| A mixed composition of a compound prepared in Preparation Example 1 and metformin | 100 mg |
| Cornstarch | 100 mg |
| Lactose | 100 mg |
| Magnesium stearate | 2 mg |

The above ingredients were mixed, and then sealed in a gelatin capsule according to a conventional preparation method to prepare a capsule formulation.

| <1-4> Preparation of injection solution | |
|---|---|
| A mixed composition of a compound prepared in Preparation Example 1 and metformin | 10 μg/ml |
| Diluted hydrochloric acid BP added until reaching | pH 3.5 |
| Sodium chloride BP for injection | Max. 1 ml |

After dissolving 7α-aminosteroid derivative of Formula 1 in sodium chloride BP for injection having a proper volume, pH of the formed solution was adjusted to pH 3.5 with diluted hydrochloric acid BP. The volume of the solution was controlled with sodium chloride BP for injection, and then sufficiently mixed. After filling the solution into a 5 ml Type I ample made of transparent glass, the ample was sealed by melting the upper empty part of the ample, and sterilized for more than 15 minutes at 120° C. in an autoclave to prepare an injection solution.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

We claim:
1. A pharmaceutical composition for the prevention and treatment of diabetes or obesity, comprising as active ingredients:
(1) a compound represented by the following Formula 1,

<Formula 1>

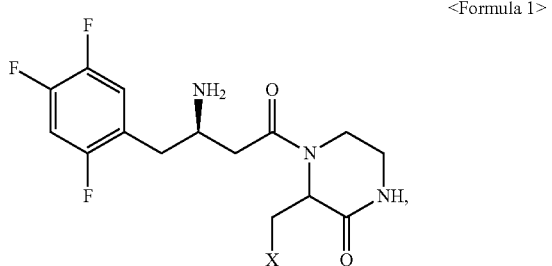

a pharmaceutically acceptable salt thereof, a hydrate thereof, or a solvate thereof, and
(2) one or more other antidiabetic or antiobesity agents, wherein X is $OR^1$, $SR^1$, or $NR^1R^2$, wherein $R^1$ and $R^2$ are independently a $C_1$~$C_5$ lower alkyl, or $R^1$ and $R^2$ of $NR^1R^2$ may form a 5-membered to 7-membered ring containing O.

2. The composition according to claim 1, wherein the compound represented by Formula 1 is selected from the group consisting of:
1) (R)-4-[(R)-3-amino-4-(2,4,5-trifluorophenyl)butanoyl]-3-(t-butoxymethyl)piperazin-2-one;
2) (S)-4-[(R)-3-amino-4-(2,4,5-trifluorophenyl)butanoyl]-3-(t-butoxymethyl)piperazin-2-one;
3) (R)-4-[(R)-3-amino-4-(2,4,5-trifluorophenyl)butanoyl]-3-(methoxymethyl)piperazin-2-one;
4) (R)-4-[(R)-3-amino-4-(2,4,5-trifluorophenyl)butanoyl]-3-(isopropoxymethyl)piperazin-2-one;
5) (R)-4-[(R)-3-amino-4-(2,4,5-trifluorophenyl)butanoyl]-3-(cyclopentyloxymethyl)piperazin-2-one;
6) (R)-4-[(R)-3-amino-4-(2,4,5-trifluorophenyl)butanoyl]-3-[(diethylamino)methyl]piperazin-2-one;
7) (R)-4-[(R)-3-amino-4-(2,4,5-trifluorophenyl)butanoyl]-3-[(ethylmethylamino)methyl]piperazin-2-one;
8) (R)-4-[(R)-3-amino-4-(2,4,5-trifluorophenyl)butanoyl]-3-(morpholinomethyl)piperazin-2-one; and
9) (R)-4-[(R)-3-amino-4-(2,4,5-trifluorophenyl)butanoyl]-3-(t-butylthiomethyl)piperazin-2-one.

3. The composition according to claim 1, wherein the pharmaceutically acceptable salt is selected from the group consisting of acetic acid, benzenesulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, maleic acid, malic acid, mandelic acid, methanesulfonic acid, mucic acid, nitric acid, pamoic acid, pantothenic acid, phosphoric acid, succinic acid, sulfuric acid, tartaric acid, p-toluene sulfonic acid, and adipic acid.

4. The composition according to claim 1, wherein the compound represented by Formula 1, the pharmaceutically acceptable salt thereof, the hydrate thereof, or the solvate thereof is a Dipeptidyl Peptidase-IV (DPP-IV) inhibitor.

5. The composition according to claim 1, wherein the other antidiabetic or antiobesity agents are selected from the group consisting of Biguanides, insulin sensitizers, insulin secretagogues, α-glucosidase inhibitors, and cannabinoid receptor-1 antagonists.

6. The composition according to claim 1, wherein the other antidiabetic or antiobesity agents are Biguanides.

7. The composition according to claim 6, wherein the Biguanide is metformin, buformin, or phenformin.

8. The composition according to claim 6, wherein the pharmaceutical composition comprises the compound represented by Formula 1 or pharmaceutically acceptable salt thereof and the Biguanide at a ratio of 9:1 to 1:3 based on respective $ED_{30}$ values thereof.

9. The composition according to claim 6, wherein the pharmaceutical composition comprises the compound represented by Formula 1 or pharmaceutically acceptable salt thereof and the Biguanide at a ratio of 1:1 based on respective $ED_{30}$ values thereof.

10. The composition according to claim 6, wherein the pharmaceutical composition comprises 16.7 to 450 parts by weight of the Biguanide based on 1 part by weight of the compound 1 represented by Formula 1.

11. The composition according to claim 1, wherein the other antidiabetic or antiobesity agents are insulin sensitizers.

12. The composition according to claim 11, wherein the insulin sensitizer has a thiazolidin-dione (TZD) structure.

13. The composition according to claim 11, wherein the insulin sensitizer is selected from the group consisting of troglitazone, ciglitazone, rosiglitazone, pioglitazone, and englitazone.

14. The composition according to claim 11, wherein the pharmaceutical composition comprises 0.01 to 0.4 parts by weight of the insulin sensitizer based on 1 part by weight of the compound represented by Formula 1.

15. The composition according to claim 1, wherein the other antidiabetic or antiobesity agents are insulin secretagogues.

16. The composition according to claim 15, wherein the insulin secretagogue is selected from the group consisting of glybenclamide (glyburide), glipizide, gliclazide, glimepiride, tolazamide, tolbutamide, acetohexamide, carbutamide, chlorpropamide, glibornuride, gliquidone, glisentide, glisolamide, glisoxepide, glyclopyamide, glycylamide, glipentide, repaglinide, and nateglinide.

17. The composition according to claim 15, wherein the pharmaceutical composition comprises 0.2 to 3.2 parts by weight of the insulin secretagogue based on 1 part by weight of the compound represented by Formula 1.

18. The composition according to claim 1, wherein the other antidiabetic or antiobesity agents are alpha-glucosidase inhibitors.

19. The composition according to claim 18, wherein the alpha-glucosidase inhibitor is selected from the group consisting of acarbose, voglibose, emiglitate, and miglitol.

20. The composition according to claim 18, wherein the pharmaceutical composition comprises 0.03 to 0.18 parts by weight of the alpha-glucosidas inhibitor based on 1 part by weight of the compound represented by Formula 1.

21. The composition according to claim 1, wherein the other antidiabetic or antiobesity agents are cannabinoid receptor-1 antagonists.

22. The composition according to claim 21, wherein the cannabinoid receptor-1 antagonist is selected from the group consisting of Rimonabant, Otenabant, Ibinabant, and Surinabant.

23. The composition according to claim 21, wherein the pharmaceutical composition comprises 1 to 10 parts by weight of the cannabinoid receptor-1 antagonist based on 1 part by weight of the compound represented by Formula 1.

24. The composition according to claim 1, wherein the compound represented by the following Formula 1, the pharmaceutically acceptable salt thereof, the hydrate thereof, or the solvate thereof, and the other antidiabetic or antiobesity agents are pre-mixed for formulation or separately formulated.

25. The composition according to claim 1, wherein the pharmaceutical composition is formulated to be orally administered.

* * * * *

UNITED STATES PATENT AND TRADEMARK OFFICE
CERTIFICATE OF CORRECTION

PATENT NO. : 8,440,669 B2  
APPLICATION NO. : 13/124150  
DATED : May 14, 2013  
INVENTOR(S) : Shin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 128 days.

Signed and Sealed this
Eighth Day of September, 2015

Michelle K. Lee
*Director of the United States Patent and Trademark Office*